United States Patent [19]

Berryman et al.

[11] Patent Number: 5,658,943
[45] Date of Patent: Aug. 19, 1997

[54] PHENYLALANINE DERIVATIVES AS ENDOTHELIN ANTAGONISTS

[75] Inventors: Kent Alan Berryman; Xue-Min Cheng; Annette Marian Doherty, all of Ann Arbor; Jeremy John Edmunds, Ypsilanti; Sylvester Klutchko, Ann Arbor, all of Mich.

[73] Assignee: Warner-Lambert Company, Morris Plains, N.J.

[21] Appl. No.: 369,209

[22] Filed: Jan. 5, 1995

[51] Int. Cl.$^6$ .................. C07C 229/36; C07C 229/30; C07C 317/60

[52] U.S. Cl. .................. 514/466; 514/538; 514/539; 514/562; 514/563; 514/567; 514/63; 514/617; 514/464; 560/40; 562/439; 562/446; 549/435; 549/444; 556/419

[58] Field of Search ................... 562/439, 446; 560/40; 549/435, 444; 514/466, 538, 539, 562, 563, 567, 63; 556/419

[56] References Cited

U.S. PATENT DOCUMENTS

| | | |
|---|---|---|
| 3,714,241 | 1/1973 | Grenda ........................ 560/40 |
| 3,930,017 | 12/1975 | Kummer et al. ............... 560/40 |
| 4,497,964 | 2/1985 | Ojima et al. ................... 562/406 |
| 5,198,548 | 3/1993 | Beylin et al. .................. 546/136 |
| 5,246,943 | 9/1993 | Blankley et al. .............. 560/40 |

FOREIGN PATENT DOCUMENTS

| | | |
|---|---|---|
| 0522808A2 | 1/1993 | European Pat. Off. . |
| 93/01159 | 1/1993 | WIPO . |
| 93/01165 | 1/1993 | WIPO . |
| 93/01169 | 1/1993 | WIPO . |

OTHER PUBLICATIONS

Davies et al., CA 118:81342 (1993), registry No. 90656–96–5.
Nie et al., CA 116:255995 (1992), registry No. 141523–18–4.
Lavin et al., CA 114:75177 (1991), registry No. 131930–02–4.
Hansen et al., CA 102:149743 (1985), registry No. 94732–12–4.
Somack et al., CA 96:28824 (1982), registry Nos. 80248–16–4, 80248–17–5, 80248–20–0 and 80248–21–1.
Gosteli, CA 77:114271 (1972), registry No. 36943–43–8.
Kirby et al., CA 76:59149 (1972), registry No. 35175–72–5.
Mukherjee et al., CA 75:5371 (1971), registry No. 32299–75–5.
Matsuura et al., CA 72:44093 (1970), registry No. 24956–73–8.
Matsuura et al., CA 69:52461 (1968), registry No. 19103–40–3.
Block, CA 67:108980 (1967), registry Nos. 15962–67–1 and 15962–69–3.
S. Klutchko, et al., *Bioorganic & Medicinal Chemistry Letters*, 1994, 4:1, 57–62.

Primary Examiner—Johann Richter
Assistant Examiner—Laura L. Stockton
Attorney, Agent, or Firm—Elizabeth M. Anderson

[57] ABSTRACT

Novel antagonists of endothelin are described, as well as novel intermediates used in their preparation, methods for the preparation and pharmaceutical compositions of the same, which are useful in treating elevated levels of endothelin, essential, renovascular, malignant and pulmonary hypertension, cerebral infarction, myocardial ischemia, cerebral ischemia, congestire heart failure and subarachnoid hemorrhage.

12 Claims, No Drawings

PHENYLALANINE DERIVATIVES AS ENDOTHELIN ANTAGONISTS

BACKGROUND OF THE INVENTION

The present invention relates to novel antagonists of endothelin useful as pharmaceutical agents, to methods for their production, to pharmaceutical compositions which include these compounds and a pharmaceutically acceptable carrier, and to pharmaceutical methods of treatment. More particularly, the compounds of the present invention are antagonists of endothelin useful in treating elevated levels of endothelin, acute and chronic renal failure, essential renovascular malignant and pulmonary hypertension, cerebral infarction and cerebral ischemia, cerebral vasospasm, cirrhosis, septic shock, congestive heart failure, endotoxic shock, subarachnoid hemorrhage, arrhythmias, asthma, preeclampsia, atherosclerotic disorders including Raynaud's disease and restenosis, angina, cancer, ischemic disease, gastric mucosal damage, hemorrhagic shock, ischemic bowel disease, diabetes, and benign prostatic hyperplasia.

Endothelin-1 (ET-1), a potent vasoconstrictor, is a 21 amino acid bicyclic peptide that was first isolated from cultured porcine aortic endothelial cells. Endothelin-1, is one of a family of structurally similar bicyclic peptides which include; ET-2, ET-3, vasoactive intestinal contractor (VIC), and the sarafotoxins (SRTXs).

Endothelin is involved in many human disease states.

Several in vivo studies with ET antibodies have been reported in disease models. Left coronary artery ligation and reperfusion to induce myocardial infarction in the rat heart, caused a 4- to 7-fold increase in endogenous endothelin levels. Administration of ET antibody was reported to reduce the size of, the infarction in a dose-depending manner (Watanabe T., et al., "Endothelin in Myocardial Infarction," Nature (Lond.) 1990;344:114). Thus, ET may be involved in the pathogenesis of congestire heart failure and myocardial ischemia (Marguiles K. B., et al., "Increased Endothelin in Experimental Heart Failure," Circulation 1990;82:2226).

Studies by Kon and colleagues using anti-ET antibodies in an ischemic kidney model, to deactivate endogenous ET, indicated the peptide's involvement in acute renal ischemic injury (Kon V., et al., "Glomerular Actions of Endothelin In vivo," J. Clin. Invest. 1989;83:1762). In isolated kidneys, preexposed to specific antiendothelin antibody and then challenged with cyclosporine, the renal perfusate flow and glomerular filtration rate increased, while renal resistance decreased as compared with isolated kidneys preexposed to a nonimmunized rabbit serum. The effectiveness and specificity of the anti-ET antibody were confirmed by its capacity to prevent renal deterioration caused by a single bolus dose (150 pmol) of synthetic ET, but not by infusion of angiotensin II, norepinephrine, or the thromboxane $A_2$ mimetic U-46619 in isolated kidneys (Perico N., et al., "Endothelin Mediates the Renal Vasoconstriction Induced by Cyclosporine in the Rat," J. Am. Soc. Nephrol. 1990;1:76).

Others have reported inhibition of ET-1 or ET-2-induced vasoconstriction in rat isolated thoracic aorta using a monoclonal antibody to ET-1 (Koshi T., et al., "Inhibition of Endothelin (ET)-1 and ET-2-Induced Vasoconstriction by Anti-ET-1 Monoclonal Antibody," Chem. Pharm. Bull. 1991;39:1295).

Combined administration of ET-1 and ET-1 antibody to rabbits showed significant inhibition of the blood pressure (BP) and renal blood flow responses (Miyamori I., et al., Systemic and Regional Effects of Endothelin in Rabbits: Effects of Endothelin Antibody," Clin. Exp. Pharmacol. Physiol. 1990;17:691).

Other investigators have reported that infusion of ET-specific antibodies into spontaneously hypertensive rats (SHR) decreased mean arterial pressure (MAP), and increased glomerular filtration rate and renal blood flow. In the control study with normotensive Wistar-Kyoto rats (WKY), there were no significant changes in these parameters (Ohno A., Effects of Endothelin-Specific Antibodies and Endothelin in Spontaneously Hypertensive Rats," J. Tokyo Women's Med, Coll. 1991;61:951).

In addition, elevated levels of endothelin have been reported in several disease states (see Table I below).

Burnett and co-workers recently demonstrated that exogenous infusion of ET (2.5 ng/kg/mL) to anesthetized dogs, producing a doubling of the circulating concentration, did have biological actions (Lerman A., et al., "Endothelin has Biological Actions at Pathophysiological Concentrations," Circulation 1991;83:1808). Thus heart rate and cardiac output decreased in association with increased renal and systemic vascular resistances and antinatriuresis. These studies support a role for endothelin in the regulation of cardiovascular, renal, and endocrine function.

In congestive heart failure in dogs and humans, a significant 2- to 3-fold elevation of circulating ET levels has been reported (Rodeheffer R. J., et al., "Circulating Plasma Endothelin Correlates With the Severity of Congestlye Heart Failure in Humans," Am. J. Hypertension 1991;4:9A).

The distribution of the two cloned receptor subtypes, termed $ET_A$ and $ET_B$, have been studied extensively (Arai H., et al., Nature 1990;348:730, Sakurai, T., et al., Nature 1990;348:732). The $ET_A$, or vascular smooth muscle receptor, is widely distributed in cardiovascular tissues and in certain regions of the brain (hin H. Y., et al., Proc. Natl, Acad, Sci. 1991;88:3185). The $ET_B$ receptor, originally cloned from rat lung, has been found in rat cerebellum and in endothelial cells, although it is not known if the $ET_B$ receptors are the same from these sources. The human ET receptor subtypes have been cloned and expressed (Sakamoto A., et al., Biochem, Biophys. Res, Chem. 1991;178:656, Hosoda K., et al., FEBS Lett. 1991;287:23). The $ET_A$ receptor clearly mediates vasoconstriction and there have been a few reports implicating the $ET_B$ receptor in the initial vasodilatory response to ET (Takayanagi R., et al., FEBS Lett. 1991;282:103). However, recent data has shown that the $ET_B$ receptor can also mediate vasoconstriction in some tissue beds (Panek R. L., et al., Biochem. Biophys. Res. Commun. 1992;183(2):566).

A recent study showed that selective $ET_B$ agonists caused only vasodilation in the rat aortic ring, possibly through the release of EDRF from the endothelium (ibid). Thus, reported selective $ET_B$ agonists, for example, the linear analog ET[1, 3,11,15-Ala] and truncated analogs ET[6-21,1,3,11,15-Ala], ET[8-21,11,15-Ala], and N-Acetyl-ET[10-21,11,15-Ala] caused vasorelaxation in isolated, endothelium-intact porcine pulmonary arteries (Saeki T., et al., Biochem. Biophys. Res. Commun. 1991;179:286). However, some ET analogs are potent vasoconstrictors in the rabbit pulmonary artery, a tissue that appears to possess an $ET_B$, nonselective type of receptor (ibid).

Plasma endothelin-1 levels were dramatically increased in a patient with malignant hemangioendothelioma (Nakagawa K., et al., Nippon Hifuka Gakkai Zasshi 1990;100:1453–1456).

The ET receptor antagonist BQ-123 has been shown to block ET-1 induced bronchoconstriction and tracheal smooth muscle contraction in allergic sheep providing evidence for expected efficacy in bronchopulmonary diseases such as asthma (Noguchi, et al., *Am. Rev. Respir. Dis*, 1992;145(4 Part 2):A858).

Circulating endothelin levels are elevated in women with preeclampsia and correlate closely with serum uric acid levels and measures of renal dysfunction. These observations indicate a role for ET in renal constriction in preeclampsia (Clark B. A., et al., *Am. J. Obstet. Gynecol.* 1992;166:962–968).

Plasma immunoreactive endothelin-1 concentrations are elevated in patients with sepsis and correlate with the degree of illness and depression of cardiac output (Pittett J., et al., *Ann Surg*, 1991;213(3):262).

In addition the ET-1 antagonist BQ-123 has been evaluated in a mouse model of endotoxic shock. This $ET_A$ antagonist significantly increased the survival rate in this model (Toshiaki M., et al., 20.12.90. EP 0 436 189 A1).

Endothelin is a potent agonist in the liver eliciting both sustained vasoconstriction of the hepatic vasculature and a significant increase in hepatic glucose output (Gandhi C. B., et al., *Journal of Biological Chemistry* 1990;265(29): 17432). In addition, increased levels of plasma ET-1 have been observed in microalbuminuric insulin-dependent diabetes mellitus patients indicating a role for ET in endocrine disorders such as diabetes (Collier A., et al., *Diabetes Care* 1992;15(8):1038).

$ET_A$ antagonist receptor blockade has been found to produce an antihypertensive effect in normal to low renin models of hypertension with a time course similar to the inhibition of ET-1 pressor responses (Basil M. K., et al., *J. Hypertension* 1992; 10-(Suppl 4):S49). The endothelins have been shown to be arrhythmogenic, and to have positive chronotropic and inotropic effects, thus ET receptor blockade would be expected to be useful in arrhythmia and other cardiovascular disorders (Han S.-P., et al., *Life Sci*, 1990;46:767).

The widespread localization of the endothelins and their receptors in the central nervous system and cerebrovascular circulation has been described (Nikolov R. K., et al., *Drugs of Today* 1992;28(5):303–310). Intracerebroventricular administration of ET-1 in rats has been shown to evoke several behavioral effects. These factors strongly suggest a role for the ETs in neurological disorders. The potent vasoconstrictor action of Ets on isolated cerebral arterioles suggests the importance of these peptides in the regulation of cerebrovascular tone. Increased ET levels have been reported in some CNS disorders, i.e., in the CSF of patients with subarachnoid hemorrhage and in the plasma of women with preeclampsia. Stimulation with ET-3 under conditions of hypoglycemia have been shown to accelerate the development of striatal damage as a result of an influx of extracellular calcium. Circulating or locally produced ET has been suggested to contribute to regulation of brain fluid balance through effects on the choroid plexus and CSF production. ET-1 induced lesion development in a new model of local ischemia in the brain has been described.

Circulating and tissue endothelin immunoreactivity is increased more than twofold in patients with advanced atherosclerosis (Lerman A., etal., *New England J. Med.* 1991;325:997–1001). Increased endothelin immunoreactivity has also been associated with Buerger's disease (Kanno K., etal., *J. Amer. Med, Assoc.* 1990;264:2868) and Raynaud's phenomenon (Zamora M. R., et al., *Lancet* 1990;336:1144–1147).

An increase of circulating endothelin levels was observed in patients that underwent percutaneous transluminal coronary angioplasty (PTCA) (Tahara A., et al., *Metab. Clin. Exp*, 1991;40:1235–1237).

Increased plasma levels of endothelin have been measured in rats and humans (Stewart D. J., et al., *Ann. Internal Medicine* 1991;114:464–469) with pulmonary hypertension.

Elevated levels of endothelin have also been measured in patients suffering from ischemic heart disease (Yasuda M., et al., *Amer. Heart J, 1990;119:801–806*) and either stable or unstable angina (Stewart J. T., et al., *Br. Heart J.* 1991;66:7–9).

Infusion of an endothelin antibody 1 hour prior to and 1 hour after a 60 minute period of renal ischaemia resulted in changes in renal function versus control. In addition, an increase in glomerular platelet-activating factor was attributed to endothelin (Lopez-Farre A., et al., *J. Physiology* 1991;444:513–522). In patients with chronic renal failure as well as in patients on regular hemodialysis, treatment mean plasma endothelin levels were significantly increased (Stockenhuber F., et al., *Clin. Sci.* (Lond.) 1992;82:255–258).

Local intra-arterial administration of endothelin has been shown to induce small intestinal mucosal damage in rats in a dose-dependent manner (Mirua S., et al., *Digestion* 1991;48:163–172). Furthermore, it has been shown that an anti-ET-1 antibody reduced ethanol-induced vasoconstriction in a concentration-dependent manner (Masuda E., et al., *Am. J. Physiol,* 1992;262:G785–G790). Elevated endothelin levels have been observed in patients suffering from Crohn's disease and ulcerative coliris (Murch S. H., et al., *Lancet* 1992;339:381–384).

The nonpeptide endothelin antagonist RO 46-2005 has been reported to be effective in models of acute renal ischemia and subarachnoid hemorrhage in rats (Clozel M., et al., "Pathophysiological role of endothelin revealed by the first orally active endothelin receptor antagonist," *Nature*, 1993;365:759). In addition, the $ET_A$ antagonist BQ-123 has been shown to prevent early cerebral vasospasm following subarachnoid hemorrhage (Clozel M. and Watanabe H., *Life Sci.* 1993;52:825–834).

Most recently an $ET_A$ selective antagonist demonstrated an oral antihypertensive effect (Stein P. D., et al., "The Discovery of Sulfonamide Endothelin Antagonists and the Development of the Orally Active $ET_A$ Antagonist 5-(Dimethylamino)-N-(3,4-dimethyl-5-isoxazolyl)-1-naphthalenesulfonamide, "*J. Med. Chem.,* 1994;37:329–331).

Furthermore, a specific $ET_A/ET_B$ receptor antagonist (see WO93 08799A1 and Elliott J. D., et al., *J. Med. Chem.,* 1994;37:1553–7) has demonstrated reduced neointimal formation after angioplasty (Douglas S. A., et al., *Circ. Res.,* 1994;75:190–7).

Furthermore, a specific $ET_A/ET_B$ receptor antagonist, SB 209670 (Elliott J. D., et al., *J. Med. Chem.,* 1994;37(11): 1553–7) has demonstrated reduced neointimal formation after angioplasty (Douglas S. A., et al., *Circ. Res.,* 1994;75 (1):190–7).

TABLE I

Plasma Concentrations of ET-1 in Humans

| Condition | Normal Control | ET Plasma Levels Reported (pg/mL) |
| --- | --- | --- |
| Atherosclerosis | 1.4 | 3.2 pmol/L |
| Surgical operation | 1.5 | 7.3 |
| Buerger's disease | 1.6 | 4.8 |
| Takayasu's arteritis | 1.6 | 5.3 |

TABLE I-continued

Plasma Concentrations of ET-1 in Humans

| Condition | Normal Control | ET Plasma Levels Reported (pg/mL) |
|---|---|---|
| Cardiogenic shock | 0.3 | 3.7 |
| Congestive heart failure (CHF) | 9.7 | 20.4 |
| Mild CHF | 7.1 | 11.1 |
| Severe CHF | 7.1 | 13.8 |
| Dilated cardiomyopathy | 1.6 | 7.1 |
| Preeclampsia | 10.4 pmol/L | 22.6 pmol/L |
| Pulmonary hypertension | 1.45 | 3.5 |
| Acute myocardial infarction | 1.5 | 3.3 |
| (several reports) | 6.0 | 11.0 |
|  | 0.76 | 4.95 |
|  | 0.50 | 3.8 |
| Subarachnoid hemorrhage | 0.4 | 2.2 |
| Crohn's Disease | 0–24 fmol/mg | 4–64 fmol/mg |
| Ulcerative colitis | 0–24 fmol/mg | 20–50 fmol/mg |
| Cold pressor test | 1.2 | 8.4 |
| Raynaud's phenomenon | 1.7 | 5.3 |
| Raynaud's/hand cooling | 2.8 | 5.0 |
| Hemodialysis | <7 | 10.9 |
| (several reports) | 1.88 | 4.59 |
| Chronic renal failure | 1.88 | 10.1 |
| Acute renal failure | 1.5 | 10.4 |
| Uremia before hemodialysis | 0.96 | 1.49 |
| Uremia after hemodialysis | 0.96 | 2.19 |
| Essential hypertension | 18.5 | 33.9 |
| Sepsis syndrome | 6.1 | 19.9 |
| Postoperative cardiac | 6.1 | 11.9 |
| Inflammatory arthritides | 1.5 | 4.2 |
| Malignant hemangioendothelioma | 4.3 | 16.2 |
|  | (after removal) |  |

WO 93/01169 covers 3-aryl-2-aminopropane derivatives of formula (I) and their salts and products

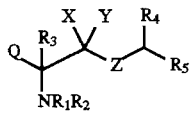

Q=phenyl, naphthyl, indoyl, benzothiophenyl, benzofuranyl, benzyl, or indazolyl, each optionally substituted;

Z=O, S, or $NR_8$;

$R_8$=H or 1-6C alkyl;

X, Y=H, or together form =O;

$R_1$, $R_2$=H, 1-6C alkyl (optionally substituted with OH, CN, CORc, $CO_2$Rc, CONRcRd, or NRcRD), phenyl (1-4C alkyl) (optionally ring-substituted by one or more of 1-6 C alkyl, 1-6C alkoxy, halo or $CF_3$), CORc, $CO_2$Rc, CONRcRd, CONRcCOORd, $SO_2$Rc;

Rc, Rd=H, 1-12C alkyl or phenyl (optionally substituted by one or more of 1-6C alkyl, 1-6C alkoxy, halo, or $CF_3$);

$R_3$=H or 1-6C alkyl;

$R_4$=H, 1-6C alkyl or phenyl (optionally substituted by 1-3 gps. chosen from 1-6C alkyl, 2-6C alkenyl, 2- 6C alkynyl, halo, CN, $NO_2$, $CF_3$, $Me_3Si$, ORa, SRa, SORa, NRaRb, NRaCORb, $NRaCO_2Rb$, $CO_2Ra$ and CONRaRb);

Ra, Rb=H, 1-6C alkyl, Ph, or $CF_3$;

$R_5$=phenyl (optionally substituted by 1-3 gps as described above for the phenyl gr $R_4$).

The compounds are disclosed as especially useful in the treatment of pain or nociception, inflammation, migraine, and posthepatic neuralgia.

WO 93/01165 covers 2-aryl-2-amino ethane derivatives of formula (I) and their salts or prodrugs

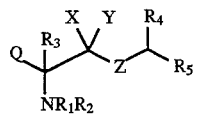

Q=optionally substituted Ph, heteroaryl, or naphthyl;

X, Y=H, 1-6C alkyl, 2-6C alkenyl or X+Y=O;

Z=O or S;

$R_1$=H, 1-6C alkyl (optionally substituted with OH, CN, CORa, COORa, CONRaRb, CO(1-4C)alkyl NRaRb, CONRa(1-4C) alkyl CONRaRb or NRaRb), phenyl (1-4C)alkyl (optionally substituted in the Ph ring by one or more of Q);

Q=1-6C alkyl, 1-6C alkoxy, halo, or $CF_3$, 2-6C alkylene, CORa, COORa, CONERa, CO(1-6C) alkylhalo, CO (1-6C) - alkylNRaRb, or CONRa (1- 6C) alkylCONRaRb;

Ra, Rb=H, 1-6C alkyl or Ph or phenyl(1-4C)alkyl both optionally ring substituted by Q;

$R_2$=$R_1$ but is not H; or $R_1$+$R_2$=a chain $(CH_2)_p$ optionally substituted by OXO, and in which one $CH_2$ gp. is optionally replaced with O or NRx;

p=4 or 5;

Rx=H or 1-6C alkyl $R_3$=H or 1-6C alkyl;

$R_4$=H, 1-6C alkyl or Ph (optionally substituted by one or more of Q);

$Q^1$=1-6C alkyl, 2-6C alkenyl, 2-6 alkynyl halo, CN, $NO_2$, $CF_3$, $SiMe_3$, SRc, SORc, $SO_2Rc$, ORc, NRcRd, NRcCORd, NRcCOORd, COORc, or CONRcRd);

Rc, Rd=H, 1-6C alkyl, Ph, or $CF_3$;

$R_5$=$(CH_2)_q$ phenyl.

The compounds are disclosed as useful for treating pain, inflammation, anxiety, psychosis, schizophrenia, dementia, Downs syndrome, demyelinating diseases, respiratory diseases, allergy, etc.

WO 93/01159 covers fused tricyclic derivatives of formula (I) and their salts and prodrugs

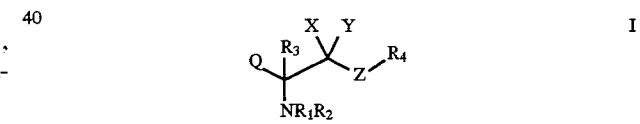

Q=a group of formula (i) in which one or both of the Ph rings can be replaced by a heteroaryl moiety;

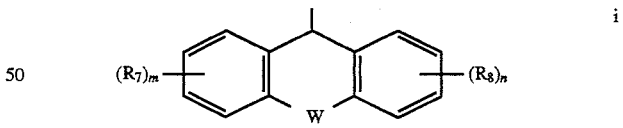

W=a bond, O, S, $CH_2CH_2$, CH=CH, or $NR_6$;

X,Y=H; or

X+Y=O;

$R_6$=H or 1-6C alkyl

Z=O, S, or $NR_6$;

$R_1$, $R_2$=N, 1-6C alkyl (optionally substituted by OH, CN, CORa, COORa, CONRaRb, CO(1-4C)alkyl NRaRb, CONRa(1-4C)alkyl CONRaRb, or NRaRb) phenyl (1-4C)alkyl (optionally substituted by one or more Q), 2-6Calkylene, CO(1-6C)alkylhalo, CORa, COORa, CONHRa, CO(1-4C)alkyl NRaRb, or CONRa(1-4C)alkyl CONRaRb; or $R_1$+$R_2$=form a chain $(CH_2)_p$ in which one nonterminal $CH_2$ group is optionally replaced with O or $NR_6$;

Q=1-6C alky, 1-6C alkoxy, halo, or $CF_3$;

p=4 or 5;
Ra,Rb=H, 1-6C alkyl or Ph or phenyl (1-4C)alkyl (both optionally ring substituted by Q);
R₃=H or 1-6C alkyl
R₄=H, 1-6C alkyl or Ph (optionally substituted by one or more of Q¹);
Q¹=1-6C alkyl, 3-6C alkenyl, 2-6C alkynyl, halo, CN, NO₂, CF₃, SiMe, SRc, SORc, S02Rc, ORc, NRcRd, RcCORd, NRcCOORd, COORc, or CONRcRd;
Rc,Rd=H, 1-6C alky, Ph, or CF₃;
R₅=(CH₂)$_q$ phenyl (optionally ring substituted by one ore more Q¹);
q=0, 3;
R₇, R₈=n, RP, Q₁;
m, n=0 to 4.

The compounds are disclosed as useful for treating pain, inflammation, anxiety, psychosis, schizophrenia, dementia, Downs syndrome, demyelinating diseases, respiratory diseases, allergy, etc.

EPA522808 discloses compounds of formula (I), and salts and products thereof:

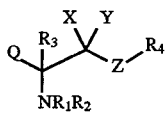

I wherein
Q is R₉CR₁₀R₁₁ or CH₂R₉CR₁₀R₁₁ where R₉ is H or OH and R₁₀ and R₁₁ are optionally substituted benzyl, C₅₋₇cycloalkyl, or (C₅₋₇ cycloalkyl)methyl;
R₁ and R₂ are H, optionally substituted C₁₋₆ alkyl, optionally substituted phenyl(C₁₋₄ alkyl), C₂₋₆ alkenyl, C₂₋₆ alkynyl, COR$^a$, COOR$^a$, COC₁₋₆alkylhalo, COC₁₋₆alkylNR$^a$R$^b$, CON-R¹²C₁₋₆alkylCONR$^a$R$^b$, CONR$^a$R$^b$, or SO₂R$^a$, or R¹ and R² together form a chain (CH₂)$_q$ optionally substituted by oxo where one methylene group may optionally be replaced by O or NR$^x$;
R³ is H, C₁₋₆alkyl, or C₂₋₆alkenyl;
R⁴ is optionally substituted phenyl(C₁₋₃alkyl);
X and Y are H, or X and Y together are=O; and
Z is O, S, or NR⁷;
are tachykinin antagonists.

The compounds are disclosed as being useful for pain, inflammation, migraine, and posttherapeutic neuralgia.

Table I below shows the plasma concentration of ET-1 in humans suffering from various conditions.

SUMMARY OF THE INVENTION

The present invention relates to novel substituted phenylalanine analogs which are endothelin antagonists of Formula I

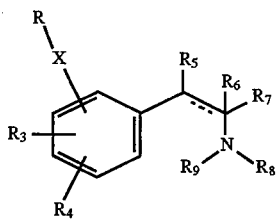

I or a pharmaceutically acceptable salt thereof wherein R, R₁-R₉, n, and X are as described below.

The present invention relates to certain compounds not previously described as potent antagonists of endothelin.

Elevated levels of endothelin have been postulated to be involved in a number of pathophysiological states including diseases associated with the cardiovascular system, as well as various metabolic and endocrinological disorders. As antagonists of endothelin, the compounds of Formula I are useful in the treatment of hypertension, cerebral ischemia and infarction, diabetes, cerebral vasospasm, cirrhosis, septic shock, congestire heart failure, endotoxic shock, subarachnoid hemorrhage, arrhythmias, asthma, chronic and acute renal failure, pre-eclampsia, atherosclerotic disorders including Raynaud's disease and restenosis, benign prostatic hyperplasia, angina, cancer, essential, renovascular, malignant and pulmonary hypertension, ischemic disease, gastric mucosal damage, hemorrhagic shock, and ischemic bowel disease.

Particularly, the compounds of Formula I are useful in treating subarachnoid hemorrhage, pulmonary hypertension, hypertension, congestire heart failure, and cerebral ischemia and/or cerebral infarction.

The compounds will be useful in cerebral ischemia or cerebral infarction resulting from a range of conditions such as thromboembolic or hemorrhagic stroke, cerebral vasospasm, head injury, hypoglycemia, cardiac arrest, status epilepticus, perinatal asphyxia, anoxia such as from drowning, pulmonary surgery, and cerebral trauma.

The present invention is also a pharmaceutical composition for administering a therapeutically effective amount of a compound of Formula I in admixture with a pharmaceutically acceptable carrier in unit dosage form in the treatment methods mentioned above.

Finally, the present invention is directed to novel intermediates used for the production of compounds of Formula I.

DETAILED DESCRIPTION OF THE INVENTION

The compounds of Formula I and their pharmaceutically acceptable salts are novel phenylalanine analogs. In Formula I, R is absent or

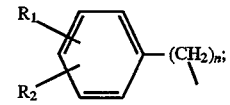

R₁ and R₂ are each independently hydrogen, lower alkyl, halogen, hydroxy, alkoxy, alkylthio, cyano, amino, alkylamino, dialkylamino, acylamino, CF₃, carboxy, carboalkoxy, hydroxyalkyl, aminoalkyl, and nitro; or R₁ and R₂ when taken together form

t=1, 2;
n is an integer of from 0 to 4;
X is absent, O, S(O)$_m$ wherein m is an integer of from 0 to 2; NH or N-alkyl;
R₃ and R₄ are each independently selected from hydrogen, alkyl, hydroxy, alkoxy, aryloxy, alkylthio, arylthio, alkylNH, dialkylN, halogen, and NH(CH₂)$_n$CO₂R',
S(CH₂)$_n$CO₂R',
O(CH₂)$_n$CO₂R',
O(CH₂)$_n$OR',
NH(CH₂)$_n$OR', and
S(CH₂)$_n$OR';

wherein R' is H or lower alkyl and w is an integer of from 1–4; or

R$_3$ and R$_4$ when taken together form

t=1,2

R$_5$ is hydrogen or YR$_{10}$ wherein Y is O, S(O)$_m$, wherein m is an integer of from 0 to 2, NH, N-alkyl, or (CH$_2$)$_p$ wherein p is an integer of from 0 to 3 and R$_{10}$ is alkyl or

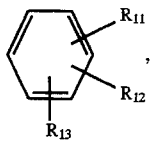

wherein R$_{11}$, R$_{12}$, and R$_{13}$ are each independently hydrogen, hydroxy, alkoxy, aralkoxy, alkyl, carboxy, and NH(CH$_2$)$_w$CO$_2$R$^1$,
S(CH$_2$)$_w$CO$_2$R$^1$,
O(CH$_2$)$_w$CO$_2$R$^1$,
O(CH$_2$)$_w$OR$^1$,
NH(CH$_2$)$_w$OR', and
S(CH$_2$)$_w$OR';

wherein R$^1$ is H or lower alkyl and w is an integer of from 1–4, or when R$_{11}$ and R$_{12}$ or R$_{12}$ and R$_{13}$ are taken together are

t=1,2;

R$_6$ is hydrogen, alkyl, alkenyl, or benzyl;

R$_7$ is hydroxyalkyl, CO$_2$R$_6$, CON(R$_6$)$_2$ wherein R$_6$ is as above, NHSO$_2$alkyl, NHSO$_2$CF$_3$, NHSO$_2$aryl, SO$_3$R$_9$, PO$_3$R$_9$ wherein R$_9$ is as defined below, CONHSO$_2$alkyl, CONHSO$_2$aryl, CONH-tetrazole, or tetrazole;

R$_8$ is hydrogen, alkyl, aryl, aralkyl, heteroaryl, COR$_{14}$ wherein R$_{14}$ is alkyl, aryl,

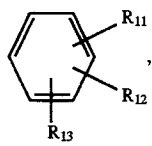

aralkyl, diaralkyl, OR$_{15}$, NR$_{15}$R$_{16}$, wherein R$_{15}$ and R$_{16}$ are each independently hydrogen, alkyl, cycloalkyl, aryl, or aralkyl; or SO$_2$R$_{14}$ wherein RH is as described above, and R$_{11}$, R$_{12}$, and R$_{13}$ are as defined above;

R$_9$ is hydrogen, alkyl, or

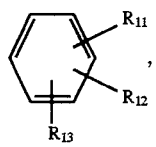

wherein
R$_{11}$, R$_{12}$, and R13 are as defined above;
- - - - indicates a double bond may be present and either regioisomer can be present.

Preferred compounds of the invention are those of Formula I wherein:

R$_1$ and R$_2$ are each independently hydrogen, lower alkyl, alkoxy, alkylthio, amino, dimethylamino,

t=1,2 and nitro;

n is an integer of from 0 to 3;

X is absent, O, S, or NH;

R$_3$ and R$_4$ are each independently hydrogen, alkoxy, aryloxy, or halogen or when taken together R$_3$ and R$_4$ form

t=1,2;

R$_5$ is hydrogen, YR$_{10}$ wherein Y is S, (CH$_2$)$_p$ wherein p is 0 and R$_{10}$ is methylenedioxyphenyl or 3-methoxyphenyl;

R$_6$ is hydrogen or methyl;

R$_7$ is hydroxyalkyl or CO$_2$R$_6$;

R$_8$ is COR$_{14}$ where R$_{14}$ is diphenylmethyl, 3,4-methylene-dioxyphenyl, phenylcyclopentyl-methyl, or NR$_{15}$R$_{16}$ where R$_{15}$ and R$_{16}$ are aryl, substituted aryl, R$_8$ is also diaralkyl or SO$_2$R$_{14}$; and R$_9$ is hydrogen.

More preferred compounds of the invention are those of Formula I wherein

R$_1$ and R$_2$ are each independently hydrogen, methoxy, or nitro;

n is an integer of from 0 to 3;

X is 0;

R$_3$ and R$_4$ are each independently hydrogen, methylenedioxy, or methoxy;

R$_5$ is hydrogen, 3,4-methylenedioxyphenyl, 3,4-dimethoxyphenyl, 3-benzyloxy-4-methoxyphenyl, or 3-methoxyphenylthio;

R$_6$ is hydrogen or methyl;

R$_7$ is COOH;

R$_8$ is COR$_{14}$ where R$_{14}$ is diphenylmethyl, 3,4-methylenedioxyphenyl, phenylcyclopentylmethyl, or NR$_{15}$R$_{16}$ where R$_{15}$ and R$_{16}$ are phenyl, R$_8$ is also 1,1-diphenylethyl or 4-isopropyl-benzenesulfonyl; and R$_9$ is hydrogen.

Other preferred compounds of the invention are those of Formula I wherein R and X are both absent.

Still more preferred compounds of the invention are:

(R,S)-3-Methoxy-2-(phenylmethoxy)phenylalanine, ethyl ester, hydrochloride (intermediate);

(R,S)-3-(2-Benzyloxy-3-methoxyphenyl)-2-diphenylacetylaminopropionic acid, ethyl ester;

(R,S)-N-(Diphenylacetyl)-3-methoxy-2-(phenylmethoxy) phenylalanine;

(R,S)-2-Diphenylacetylamino-3-[3-methoxy-2-(2-phenylethoxy)phenyl]propionic acid;

(R,S)-3-(2-Benzyloxy-3-methoxyphenyl)-2-(3,3-diphenylureido)propionic acid;

(R,S)-Diphenylacetylamino-3-[3-methoxy-2-(3-phenylpropoxy)phenyl]propionic acid;

(R,S)-2-Diphenylacetylamino-3-[3-methoxy-2(4-nitrophenoxy)phenyl]propionic acid;

(R,S)-3-(2-Benzyloxy-3-methoxyphenyl)-2-(3-naphthalen-1-yl-2-naphthalen-1-ylmethylpropionylamino) propionic acid;

(R,S; R,S)-3-(2-Benzyloxy-3-methoxyphenyl)-2-(2-cyclopentyl-2-phenyl-acetylamino)propionic acid;

(R,S)-3-(2-Hydroxyphenyl)-2-diphenylacetylalminopropionic acid, methyl ester;

(R,S)-3-(2-Benzyloxyphenyl)-2-diphenylacetylaminopropionic acid;

(R,S; R.S)-3-Benzo[1,3]dioxol-5-yl-3-(3-benzyloxy-4-methoxyphenyl)-2-diphenyl-acetylaminopropionic acid;

(R,S; R,S)-2-Diphenylacetylamino-3-(3-methoxyphenyl)-3-(3-methoxyphenyl-sulfanyl)propionic acid;

(R,S)-N-[2-(2-Benzyloxy)-3-methoxyphenyl)-1-hydroxymethylethyl]-2,2-diphenylacetamide;

(R,S)-3-(2-Benzyloxy-3-methoxyphenyl)-2-(2,2-diphenylethylamino)propionic acid;

3,3-Bis-benzo[1,3]dioxol-5-yl-2-diphenyl-acetylaminopropionic acid;

(R,S; R,S)-3-Benzo[1,3]dioxol-5-yl-3-(3-benzyloxy-4-methoxyphenyl)-2-diphenyl-acetylaminopropionic acid; and (R,S; R,S)-2-Diphenylacetylamino-3-(3-methoxyphenyl)-3-(3-methoxyphenyl-sulfanyl)propionic acid.

Novel intermediates useful in the preparation of final products are:

3,3 -Bis-benzo [1,3]dioxol -5-yl -2-nitropropionic acid, ethyl ester;

2-Amino -3,3-bis-benzo[1,3]dioxol-5-yl-propionic acid, ethyl ester;

3,3-Bis-benzo[1,3]dioxol-5-yl -2-diphenyl-acetylaminopropionic acid, ethyl ester;

(R,S)-2-Amino-3-(2-benzyloxy-3-methoxyphenyl)-2-methylpropionic acid, ethyl ester;

(R,S)-3-(2-Benzyloxy-3-methoxyphenyl)-2-diphenylacetylamino-2-methylpropionic acid;

2-tert-Butoxycarbonylamino-3-(3-methoxyphenyl) acrylic acid, methyl ester;

(R,S; R,S)-2-tert-Butoxycarbonylamino-3-(3-methoxyphenyl)-3-(3-methoxyphenyl-sulfanyl)-propionic acid, methyl ester;

(R,S; R,S)-2-Amino-3-(3-methoxyphenyl)-3-(3-methoxyphenyl-sulfanyl)propionic acid, methyl ester; and (R,S; R,S)-2-Diphenylacetylamino-3-(3-methoxyphenyl)-3-(3-methoxyphenyl-sulfanyl) propionic acid, methyl ester.

In the compounds of Formula I, the term "alkyl" means a straight or branched hydrocarbon radical having from 1 to 12 carbon atoms unless otherwise specified and includes, for example, methyl, ethyl, n-propyl, isopropyl, n-butyl, sec-butyl, isobutyl, tert-butyl, allyl, n-pentyl, n-hexyl, n-heptyl, n-octyl, n-nonyl, n-decyl, undecyl, and dodecyl.

The term "cycloalkyl" means a saturated hydrocarbon ring which contains from 3 to 12 carbon atoms unless otherwise specified, for example, cyclopropyl, cyclobutyl, cyclopentyl, cyclohexyl, cycloheptyl, and adamantyl.

"Halogen" is fluorine, chlorine, bromine or iodine.

The term alkoxy refers to an alkyl radical attached to the reminder of the molecule by oxygen; this includes, but it not limited to, methoxy, ethoxy, and propoxy groups.

The terms alkylamino and dialkylamino refer to one or two alkyl radicals attached to a nitrogen atom; N-methylamino and N, N-dimethylamino are examples.

Acylamino includes such groups as $CH_3CONH$, $CH_3CH_2CONH$, PhCONH.

Carboalkoxy refers to groups such as alkyl esters of carboxylic acids.

Hydroxyalkyl refers to alkyl groups of from 1 to 6 carbon atoms which may be straight or branched, such as $CH_2OH$.

Aryl is an aromatic hydrocarbon such as phenyl, naphthyl, and the like. The aryl my be unsubstituted or substituted by one or more selected from alkyl such as methyl or ethyl, alkoxy such as methoxy or ethoxy, methylenedioxy, hydroxy, halogen, such as fluorine, chlorine, and bromine, $NO_2$, $NH_2$, NHalkyl, $N(alkyl)_2$, $SCH_3$, SH, $OalkylCO_2H$, $OalkylCO_2alkyl$, $SalkylCO_2H$, $SalkylCO_2alkyl$, OalkylOH, OalkylOalkyl, SalkylOH, and SalkyOalkyl.

Aralkyl and diaralkyl are as defined above for alkyl and for aryl. Such groups include, but are not limited to, $PhCH_2$—and $PH_2CH$—. The groups can be unsubstituted or substituted on the alkyl and/or on the aryl portion such as the groups

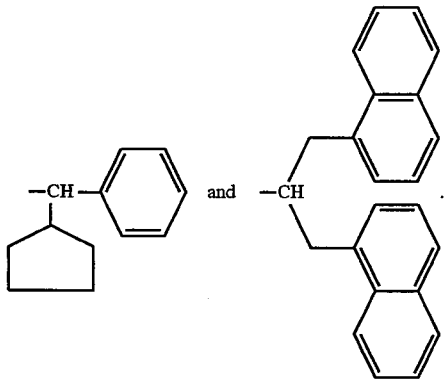

Substituents on the alkyl portion are, for example, alkyl, dialkyl, or cycloalkyl.

Aryloxy, arylthio, and alkylthio refers to groups such as, but are not limited to, PhO, PhS, and alkyls.

Alkylamino and dialkylamino refers to groups such as alkylNH and dialkylN.

Some of the compound of Formula I are capable of further forming both pharmaceutically acceptable acid addition and/or base salts. All of these forms are within the scope of the present invention.

Pharmaceutically acceptable acid addition salts of the compounds of Formula I include salts derived from nontoxic inorganic acids such as hydrochloric, nitric, phosphoric, sulfuric, hydrobromic, hydriodic, hydrofluoric, phosphorous, and the like, as well as the salts derived from nontoxic organic acids, such as aliphatic mono- and dicarboxylic acids, phenyl-substituted alkanoic acids, hydroxyalkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *Journal of Pharmaceutical Science*, 1977;66:1–19).

The acid addition salts of said basic compounds are prepared by contacting the free base form with a sufficient amount of the desired acid to produce the salt in the conventional manner.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S. M., et al., Pharmaceutical Salts," *Journal of Pharmaceutical Science* 1977;66:1–19).

The base addition salts of said acidic compounds are prepared by contacting the free acid form with a sufficient amount of the desired base to produce the salt in the conventional manner.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R or S configuration. The present invention includes all enantiomeric and epimeric forms as well as the appropriate diastereomeric mixtures thereof. Both the E- and Z-isomers are included when a double bond is present where dotted line is indicated.

The compounds of Formula I are valuable antagonists of endothelin. The tests employed indicate that compounds of the invention possess endothelin antagonist activity. Thus, the compounds were tested for their ability to inhibit [$^{125}$I]-ET-1([$^{125}$I]-Endothelin-1) binding in a receptor assay. Selected compounds were also tested for antagonist activity by inhibition of ET-1 stimulated arachidonic acid release. The following testing procedures were used (Doherty A. M., et al., "Design of C-Terminal Peptide Antagonists of Endothelin: Structure-Activity Relationships of ET-1 [16–21, D-His$^{16}$]", *Bioorganic and Medicinal Chemistry Letters* 1993;3:497–502).

Radioligand Binding Assays

The following cultured cells were used in binding experiments: rabbit renal artery vascular smooth muscle cells (ERBA-A), Ltk-cells expressing recombinant human ET$_A$R (HERBA-A), and CHO-K1 cells expressing recombinant human ET$_B$R (HERBA-B).

Membranes were prepared from cultured cells by lysing cells in cold lysis buffer (5 mM HEPES, 2 mM EDTA, pH 7.4) and homogenizing with a Dounce "A" homogenizer. The homogenate was centrifuged at 30,000×g for 20 minutes at 4° C. Membrane pellets were suspended in cold buffer containing 20 mM Tris, 2 mM EDTA, 200 µM Pefabloc, 10 µM phosphoramidon, 10 µM leupeptin, 1 µM pepstatin at pH 7.4 and frozen at −80° C. until use. Membranes were thawed and homogenized with a Brinkmann Polytron then diluted in tissue buffer containing 20 mM Tris, 2 mM EDTA, 200 µM Pefabloc and 100 µM bacitracin (pH 7.4). Radioligand and competing ligands were prepared in binding buffer containing 20 mMTris, 2 mM EDTA, and 0.1% BSA.

Competing binding assays were initiated by combining membranes, [125I]-ET-1 (40 pM) and the competing ligand in a final volume of 250 µL and incubating for 2 hours at 37° C. The assay was terminated by filtration over Whatman GF/B filters which were presoaked with 50 mM Tris, pH 7.4 containing 0.2% BSA and 100 µM bacitracin. Nonspecific binding was defined as binding in the presence of 100 nMET-1.

IN VITRO INHIBITION OF ET-1 STIMULATED ARACHIDONIC ACID RELEASE (AAR) IN CULTURED RABBIT VASCULAR SMOOTH MUSCLE CELLS (ET$_A$) AND RAT CEREBELLUM (ET$_B$) BY THE COMPOUNDS OF THE INVENTION

Antagonist activity is measured by the ability of added compounds to reduce endothelin-stimulated arachidonic acid release in cultured vascular smooth muscle cells as arachidonic acid release (AAR). [$^3$H]Arachidonic Acid Loading Media (LM) is DME/F12+0.5% FCS×0.25 mCi/mL [$^3$H]arachidonic acid (Amersham). Confluent monolayers of cultured rabbit renal artery vascular smooth muscle cells were incubated in 0.5 mL of the LM over 18 hours, at 37° C., in 5% $CO_2$. The LM was aspirated and the cells were washed once with the assay buffer (Hank's BSS+10 mM HEPES+fatty acid-free BSA (1 mg/mL)), and incubated for 5 minutes with 1 mL of the prewarmed assay buffer. This solution was aspirated, followed by an additional 1 mL of prewarmed assay buffer, and further incubated for another 5 minutes. A final 5-minute incubation was carried out in a similar manner. The same procedure was repeated with the inclusion of 10 µL of the test compound (1 nM to 1 µM) and 10 µL ET-1 (0.3 nM) and the incubation was extended for 30 minutes. This solution was then collected, 10 µL of scintillation cocktail was added, and the amount of [$^3$H] arachidonic acid was determined in a liquid scintillation counter.

The data in Table II below show the endothelin receptor binding activity of representative compounds of the instant invention.

TABLE II

| Example | ERBA-A, IC$_{50}$ µM | HERBA-A, IC$_{50}$ µM | HERBA-B, IC$_{50}$ µM | AAR-B, IC$_{50}$ µM |
|---|---|---|---|---|
| 3 | 14 | 3.4 | 2.0 | 10 |
| 4 | 16 | 3.4 | 1.0 | 6.1 |
| 7 | | 9.3 | 9.4 | |
| 8 | 17 | NA* | | |
| 14 | NA | | 23 | |
| 5 | 13 | | 6.8 | |
| 9 | NA | | 2.2 | |
| 10 | 23 | | 2.2 | |
| 16 | 7.1 | | 9.7 | |
| 21 | | 1.3 | 2.5 | |
| 38 | | 1.3 | 13 | |
| 40 | | 4 | 16 | |
| 23 | | 27 | 12 | |
| 35 | | | 1.8 | 3 |

*Not active at 25 µM

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, table, cachet, or lozenge itself, or it can be the appropriate number of any of these in packaged form.

The quantity of active component in a unit dose preparation may be varied or adjusted from 0.1 to 100 mg preferably 0.5 to 100 mg according to the particular application and the potency of the active component. The composition can, if desired, also contain other compatible therapeutic agents.

In therapeutic use as antagonists of endothelin, the compounds utilized in the pharmaceutical method of this invention are administered at the initial dosage of about 0.01 mg to about 100 mg/kg daily. A daily dose range of about 0.01 mg to about 10 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

The strategy for preparation of compounds of Formula I is exemplified in Schemes I to IV.

Acylation of the amino acid 1 under Schotten-Baumann type conditions (Scheme I) with methanol-methylene chloride as the solvent and tetramethylammoniumhydroxide as the base, offers the most direct route to the desired target Compounds 6. The yields, however, are only modest. An alternate pathway involves first esterifying the amino acid 1 using ethanolic hydrogen chloride at room temperature to give 2, and then acylation with an acid chloride in the presence of a base, preferably triethylamine, in a solvent, preferably chloroform to give Compound 3. Subsequent hydrolysis with aqueous base such as 1N sodium hydroxide in solvent such as methanol at reflux temperatures generates the free acid product 6. The R group of 6 may be varied by debenzylation of 3 with hydrogen and a catalyst, preferably 20% palladium on carbon to give an intermediate phenol 4 which in turn may be aralkylated to the intermediate ester 5 in a solvent, preferably N,N-dimethylformamide, and a base, preferably powdered potassium carbonate at room temperature for 1 to 20 hours. Subsequent aqueous base hydrolysis of 5 by a procedure similar to that for 3 to 6 yields the product 6.

Reduced amide derivatives such as 9 (Scheme I) are prepared by a reductive alkylation of antino ester 2. The imine intermediate 7 is prepared froman aldehyde, such as diphenylacetaldehyde, and the amine 2, under dehydration conditions, preferablyby the use of molecular sieves, with stirring, in a solvent, preferably 2-propanol at 25° C. for a period of 24 to 48 hours. After filtration, the reduction is carried out by first adjusting the pH of the filtrate to ca 3.5 with dropwise addition of ethereal hydrogen chloride in the presence of an indicator bromocresol green. The correct pH is achieved when the color changes from blue to green. At this time, a reducing agent, preferably sodium cyanoborohydride, is added portionwise at 25° C., with stirring, over a period from 5 to 25 minutes, adjusting the pH as necessary with ethereal hydrogen chloride during the addition.

Scheme II shows a synthesis of target compounds such as 15 that contain a phenyl group at the position β to the carboxylic acid. In the first step, the bromo methylenedioxy-benzene 10 is reacted with a strong base such a n-butyllithium in a nonprotic solvent such as tetrahydrofuran at −78° C. The resulting phenyl lithio derivative is allowed to react with piperonal at −78° to 0° to yield the benzhydrol derivative 11. Reaction of 11 with a large excess of ethyl nitro acetate neat in the presence of an acid catalyst, preferably p-toluenesulfonic acid, at elevated temperatures, preferably 100°–140° C. for 1 to 6 hours gives the nitro ester product 12. Catalytic reduction of 12 is accomplished in a solvent, preferably a mixture of ethyl acetate and methanol, with 20% palladium on carbon catalyst giving the amino ester 13. The acylation of 13 and hydrolysis of the product 14 to the target compound 15 is accomplished by conditions similar to those used to prepare Compounds 3 and 6 in Scheme I.

5,658,943
SCHEME I
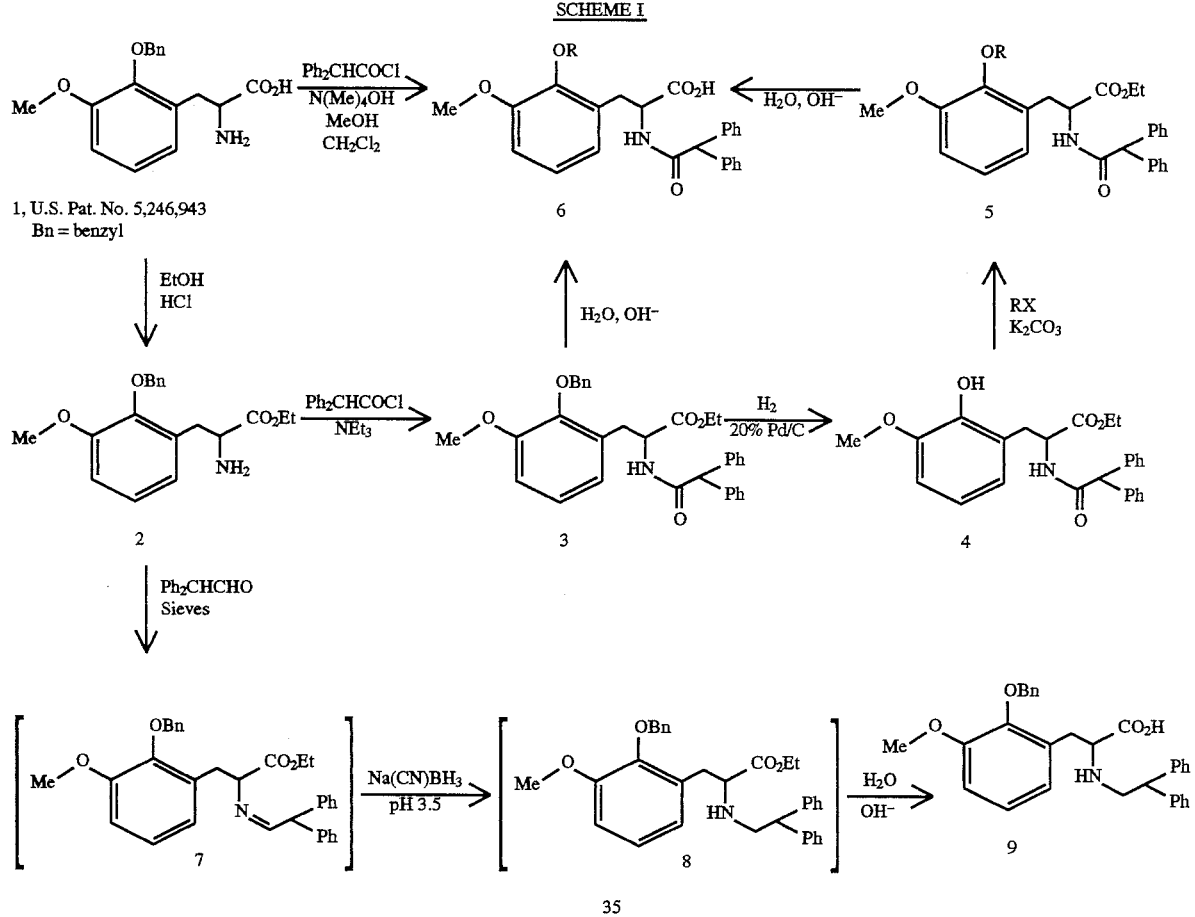
SCHEME II
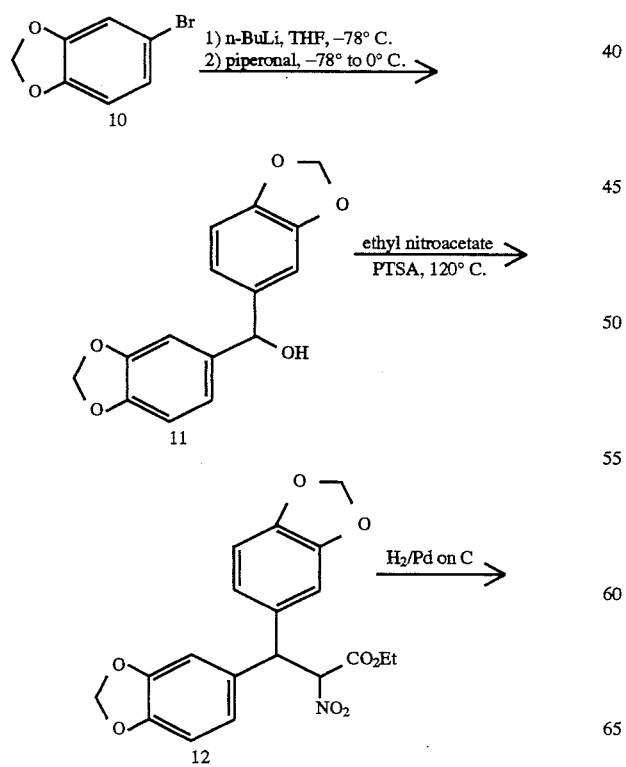
-continued
SCHEME II

-continued
SCHEME II

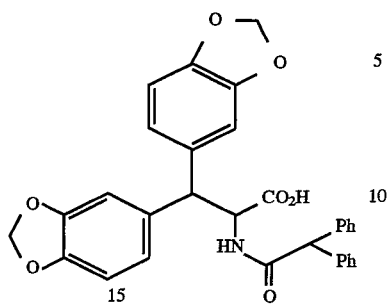

15

α-Methyltyrosine derivatives of Type 20 are synthesized as outlined in Scheme III. A schiff base 17 is formed from benzaldehyde and an amino ester base such as 2 under dehydration conditions in the presence of an acidic agent such as anhydrous magnesium sulfate in a solvent such as tetrahydrofuran for a period of 24 to 48 hours. The carbanion of the resulting schiff base product 17 is generated by addition of a solution of 17 in tetrahydrofuran to a solution of lithiumdiisopropyl amide in tetrahydro-furan at low temperatures (−20° to 0° C.) over a period of 30 to 60 minutes. To this solution is added iodomethane at −5° to 0° C. The reaction is then stirred at 25° C. for 10 to 20 hours. Hydrolysis of the α-methylated imine to the amino ester 18 is accomplished by treatment with an aqueous acid solution, preferably a 15% citric acid solution, at room temperature. Compound 18, as a free base, is acylated with an acid chloride such as diphenylacetyl chloride in the presence of a base, preferably triethylamine, to give the ester-amide 19. The ester is hydrolyzed in a solvent, preferably methanol with a strong base, preferably 1B sodium hydroxide, to yield the target e-methyltyrosine derivative 20.

Scheme IV shows a synthesis of compounds like 30 that contain a phenylthio moiety at the position β to the carboxylic acid. In the first step of the sequence, the N-Boc-glycine ester 22 is obtained by acylation of glycine, methyl ester under standard acylation conditions with di-tert-butyl dicarbonate. Bromination of 22 to compound 23 is accomplished with a brominating agent, preferably N-bromosuccinimide in a solvent, preferably carbon tetrachloride at its boiling point for a period of 1 to 6 hours. The phosphonic acid ester intermediate 24 is synthesized by treatment of 23 with trimethyl phosphite in a solvent, preferably tetrahydrofuran, at its boiling point for a period of 15 to 25 hours. The acrylic ester derivative 25 is obtained by the interaction of 24 and 3-methoxybenzaldehyde in a solvent, preferably methylene chloride, in the presence of a base, preferably DBU at room temperature for 15 to 25 hours. The next step, a Michael addition with 3-methoxy-benzenethiol in the presence of excess base, preferably piperidine, yields the phenylthio derivative 26 as a mixture of diastereomers. Removal of the Boc group of 26 with a strong acid, preferably trifluoroacetic acid, in a solvent, preferably methylene chloride, at room temperature for 30 minutes to 2 hours gives the amino ester 27 as a mixture of diastereomers. Acylation is effected by coupling the amine 27 with diphenylacetic acid in the presence of a carbodiimide derivative, preferably EDAC, and a base, preferably DMAP, in a solvent, preferably methylene chloride, at room temperature for 10 to 20 hours to give the ester 28. The next step, ester removal of 28, is designed to prevent a reverse Michael reaction that occurs with normal aqueous inorganic base hydrolysis. The procedure entails transesterification of 28 with excess 2-trimethylsilylethanol which is also the solvent, in the presence of 3 equivalents of a Lewis acid, preferably titanium(IV)isopropoxide, at 100° C. for a period of 15 to 25 hours. The resulting trimethylsilylethyl ester 29 is then cleaved in a solvent, preferably N,N-dimethylformamide, with tetrabutylammonium fluoride at room temperature for 30 minutes to yield a compound of this invention, compound 30.

SCHEME III

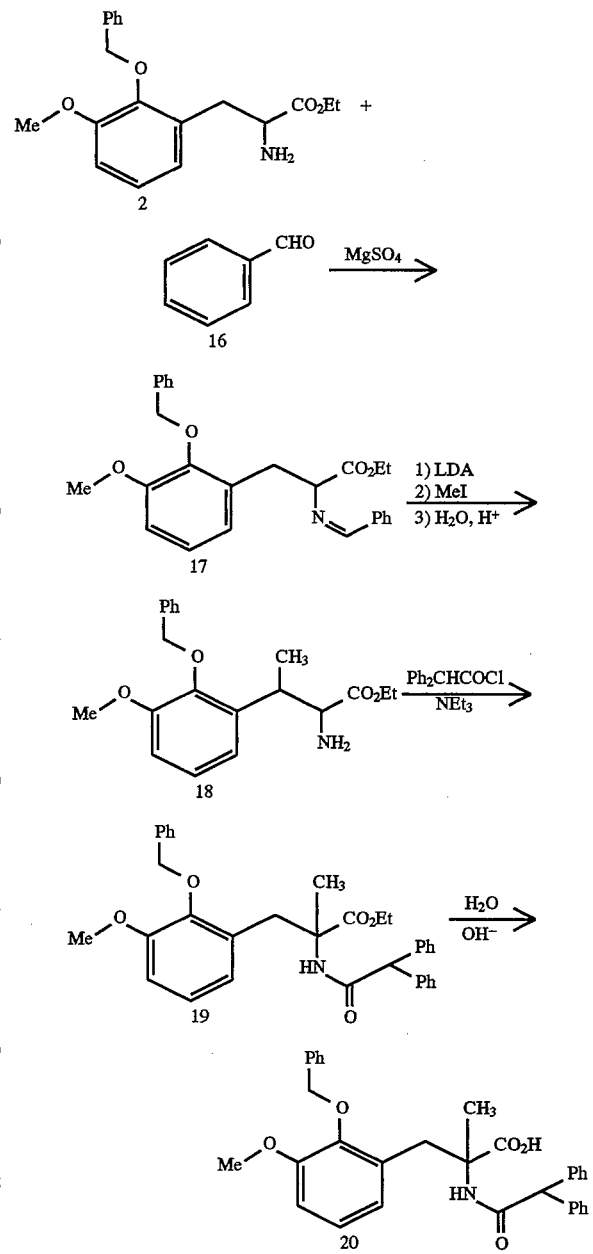

SCHEME IV

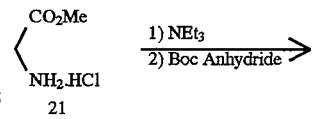

-continued
SCHEME IV

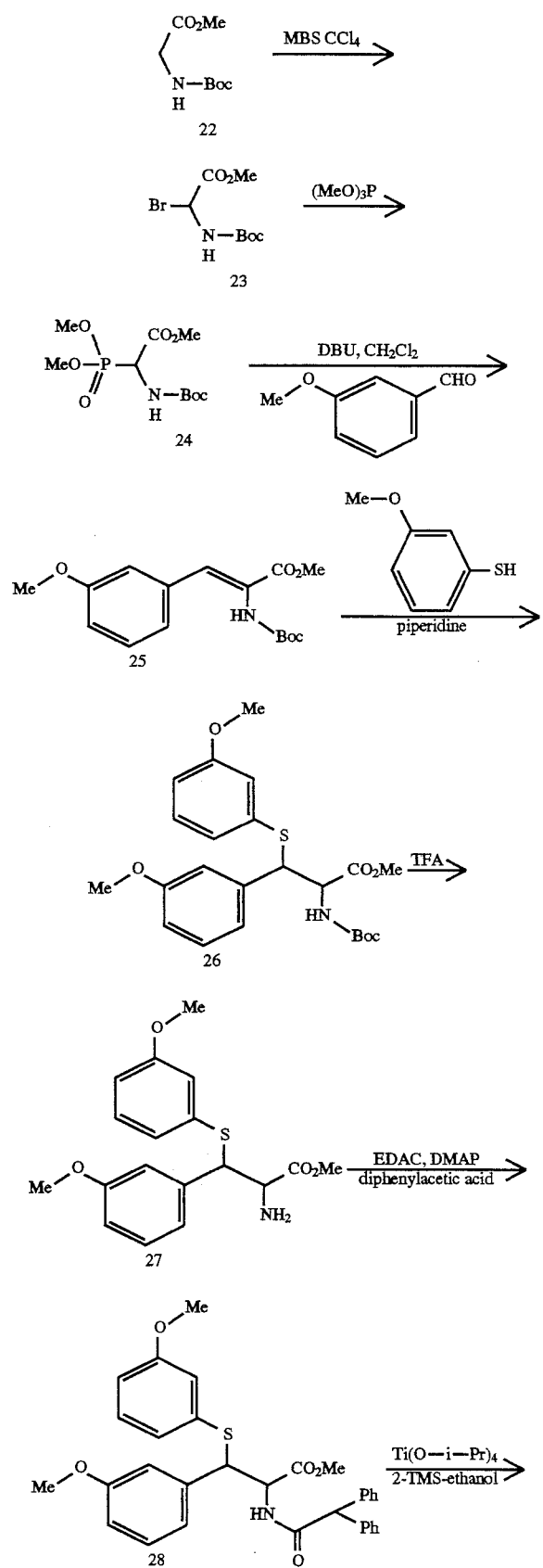

-continued
SCHEME IV

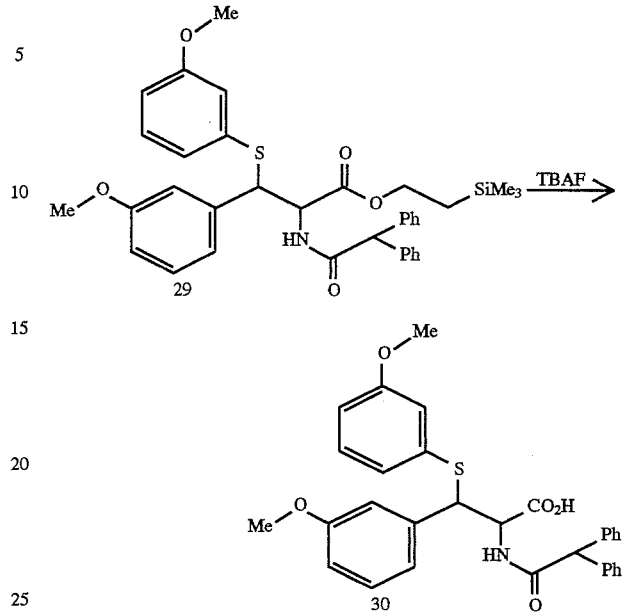

The following examples are illustrative of the instant invention; they are not intended to limit the scope in any way.

EXAMPLE 1

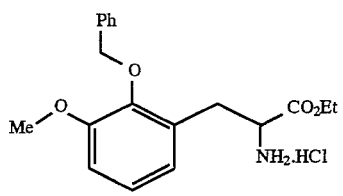

(R,S)-3-Methoxy-2-(phenylmethoxy)phenylalanine, ethyl ester, hydrochloride

Absolute ethanol (50 mL) is saturated with hydrogen chloride gas at 25° C. with cooling. A quantity of 2.50 g (8.3 mmol) of (R,S)-3-methoxy-2-(phenyl-methoxy) phenylalanine (U.S. Pat. No. 5,246,943) is added and the resulting solution is allowed to stand at room temperature for 16 hours. The solvent is evaporated and the residue is recrystallized from ethyl acetate to give pure crystalline product; mp 131°–133° C.;

Mass spectrum (CI) 330 (M$^+$+1).

Anal. Calcd for $C_{19}H_{23}NO_4 \cdot HCl$: C, 62.38; H, 6.61; N, 3.83.

Found: C, 62.00; H, 6.52; N, 3.75.

EXAMPLE 2

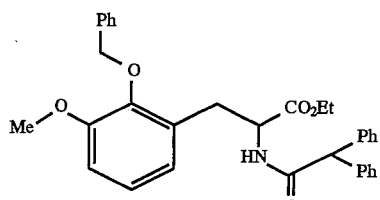

(R,S)-3-(2-Benzyloxy-3-methoxyphenyl)-2-diphenylacetyl-aminopropionic acid, ethyl ester A solution of 0.231 g (1.0 mmol) of diphenylacetyl chloride in 3.0 mL of chloroform is added over 1 minute to a stirred solution of 0.365 g (1.0 mmol) of (R,S)-3-methoxy-2-(phenylmethoxy)phenylalanine, ethyl ester, hydrochloride of Example 1, 30 mL of chloroform and 0.303 g (3.0 mmol) of triethylamine at 25° C. After 1 hour, the chloroform solution is washed with 30 mL of 2% sodium bicarbonate and then dried over anhydrous sodium sulfate. The solution is evaporated and the residual gum is dissolved in ca. 5 mL of ether. Petroleum ether is added until turbidity develops. The separated crystals are filtered; weight 0.345 g (66%); mp 82°–84° C.;

Mass spectrum (CI) 524 (M$^+$+1).

Anal. Calcd for $C_{33}H_{33}NO_5 \cdot 0.1\ H_2O$:
C, 75.43; H, 6.37; N, 2.67.

Found: C, 75.14; H, 6.13; N, 2.42.

EXAMPLE 3

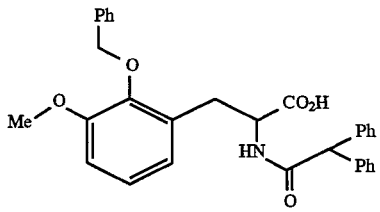

(R,S)-N-(Diphenylacetyl)-3-methoxy-2-(phenylmethoxy)-phenylalanine

A quantity of 4.55 g (0.01 mol) of 20% tetramethylammonium hydroxide-in-methanol is added to a mixture of 1.50 g (0.0041 mol) of (R,S)-3-methoxy-2-(phenylmethoxy)phenylalanine (U.S. Pat. No. 5,246,943) to give a complete solution. This solution is cooled to 0° C. With stirring, a solution of 1.115 g (0.005 mol) of diphenylacetyl chloride in 5 mL of methylene chloride is added. After 10 minutes, the solution is allowed to warm to room temperature and stirred for 1 hour. The solvent is stripped off at reduced pressure and the residue is dissolved in 50 mL of water. A volume of 25 mL of 1N hydrochloric acid is added to precipitate a gum. The gum is triturated with 10 mL of ether. The crystals that develop are filtered, washed with ether, then with water and dried; wt 1.00 g. Recrystallization from ethyl acetate gives pure product; wt 0.65 g (26%); mp 167°–168° C.

Anal. Calcd for $C_{31}H_{29}NO_5$:
C, 75.13; H, 5.90; N, 2.83.

Found: C, 75.42; H, 5.88; N, 2.77.

EXAMPLE 4

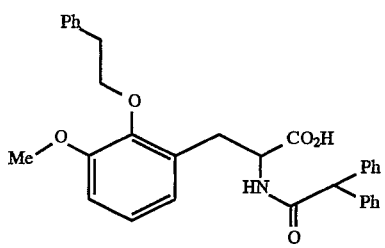

(R,S)-2-Diphenylacetylamino-3-[3-methoxy-2-(2-phenyl-ethoxy)phenyl]propionic acid This compound is made from (R,S)-3-methoxy-2-(2-phenylethoxy)phenylalanine (U.S. Pat. No. 5,246,943) and diphenylacetyl chloride by a procedure similar to that for Example 2 to give pure product; mp 138°–140° C.;

Mass spectrum (CI) 510 (M$^+$+1).

Anal. Calcd for $C_{32}H_{31}NO_5$:
C, 75.42; H, 6.13; N, 2.75.

Found: C, 75.39; H, 6.15; N, 3.03.

EXAMPLE 5

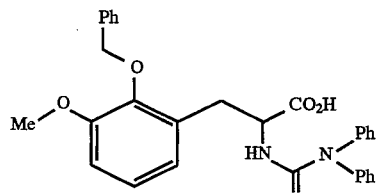

(R,S)-3-(2Benzyloxy-3-methoxyphenyl)-2-(3,3-diphenyl-ureido) propionic acid

Preparation of intermediate ester: (R,S)-3-[2-benzylxy-3-methoxhenyl)-2-(3,3-diphenylureido) propionic acid, ethyl ester is prepared by an acylation procedure similar to that for preparing (R,S)-3-(2-Benzyloxy-3-methoxyphenyl)-2-diphenylacetylamino-propionic acid, ethyl ester in Example 2 starting with 0.5 mmol of (R,S)-3-methoxy-2-(phenylmethoxy)-phenylalanine, ethyl ester, hydrochloride of Example 1, 0.5 mmol of N,N-diphenylcarbamoyl chloride, 1.5 mmol of triethyl amine, and tetrahydrofuran as a solvent. The product is obtained as a gum [mass spectrum (CI) 525 (M$^+$+1)] and is used directly in the next hydrolysis step. Hydrolysis of ester: The above prepared ester is dissolved in 15 mL of methanol. At the boiling point, a volume of 5 mL of 1N sodium hydroxide is added and the solution is maintained at reflux for 15 minutes. The methanol is evaporated and 30 mL of water is added to dissolve the separated gum. This is treated with ca. 6 mL of 1N hydrochloric acid to precipitate the free acid product which is extracted into 30 mL of ether, dried (magnesium sulfate), and evaporated. Silica gel chromatography eluting from chloroform to 1:10 methanol-chloroform yields pure product as a solid foam; tlc (2:10 methanol-chloroform) shows one spot, Rf 0.4;

Mass spectrum (CI) 496 (M$^+$).

Anal. Calcd for $C_{30}H_{28}N_2O_5$:
C, 72.56; H, 5.68; N, 5.64.

Found: C, 72.21; H, 5.53; N, 5.62.

EXAMPLE 6

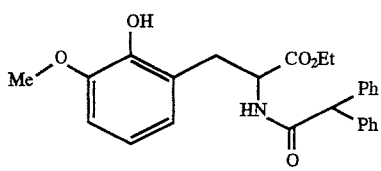

(R,S)-3-(2-Hydroxy-3-methoxyphenyl)-2-diphenylacetyl-aminopropionic acid, ethyl ester A solution of 1.00 g (1.9 mmol) of compound of Example 2 in 30 mL of methanol is hydrogenated with 130 mg of 20% palladium-on-carbon catalyst at atmospheric pressure (balloon method) for 3 hours. The catalyst is filtered and the filtrate is evaporated to give 0.80 g of pure product as gum; tlc (1:1 ethyl acetate-hexane), one spot, Rf 0.6;

Mass spectrum (CI) 434 ($M^+$+1).

EXAMPLE 7

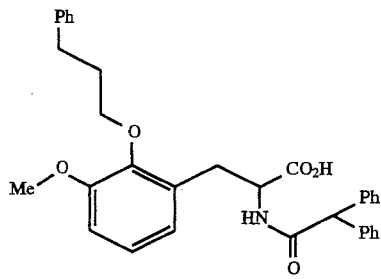

(R,S)-Diphenylacetylamino-3-[3-methoxy-2-(3-phenyl-propoxy)phenyl]propionic acid Preparation of intermediate (R,S)-diphenylacetyl-amino-3-[3-methoxy-2-(3-phenylpropoxy)phenyl]propionic acid, ethyl ester: A mixture of 0.117 g (0.27 mmol) of phenolic ester of Example 6, 0.060 g (0.3 mmol) of 3-phenylpropyl bromide, 1.0 mL of N,N-dimethylformamide and 0.5 g of powdered anhydrous potassium carbonate is stirred at 25° C. for 16 hours. Ether (5 mL) is added and the solids are filtered. The filtrate is concentrated at reduced pressure to remove most volatiles. The remaining oil is extracted into 25 mL of ether. The solution washed well with water, dried (sodium sulfate) and concentrated to give a gum; tlc (1:1 ethyl acetate-hexane), one spot Rf 0.75; Mass spectrum (CI) 552 ($M^+$+1). Base hydrolysis of above ester: The above ester is dissolved in 20 mL of hot methanol. This solution is treated with 5 mL of 1N sodium hydroxide and heated 0.5 hour on the steam bath, allowing methanol to distill over. Water (30 mL) is added to the mixture and methanol (10 mL) is added to complete the solution. A volume of 7.0 mL of 1N hydrochloric acid is added to precipitate an oil. The entire mixture is concentrated at reduced pressure and the product is extracted into 30 mL of methylene chloride. The solution is dried (magnesium sulfate), filtered, concentrated, and pumped to give a solid foam; wt 108 mg;

Mass spectrum (ES) 522 ($M^+$−1).

Anal. Calcd for $C_{33}H_{33}NO_5$.0.25 $H_2O$:

C, 75.05; H, 6.39; H, 2.65.

Found: C, 74.78; H, 5.77; N, 2.63.

EXAMPLE 8

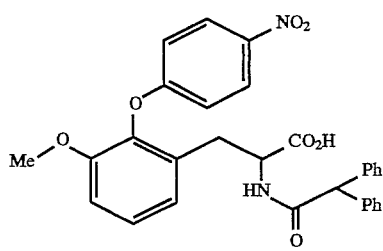

(R,S)-2-Diphenylacetylamino-3-[3-method-2-(4-nitro-phenol) phenyl]propionic acid This compound is prepared from (R,S)-3-methoxy-2-(4-nitrophenoxy)phenylalanine (U.S. Pat. No. 5,246,943) and diphenylacetyl chloride by a procedure similar to that in Example 3 to give pure product; mp 211°–213° C.;

Mass spectrum (CI) 527 ($M^+$1).

Anal. Calcd for $C_{30}H_{26}N_2O_7$.0.2 $H_2O$:

C, 67.99; H, 5.02; N, 5.29.

Found: C, 67.75; H, 5.06; N, 5.31.

EXAMPLE 9

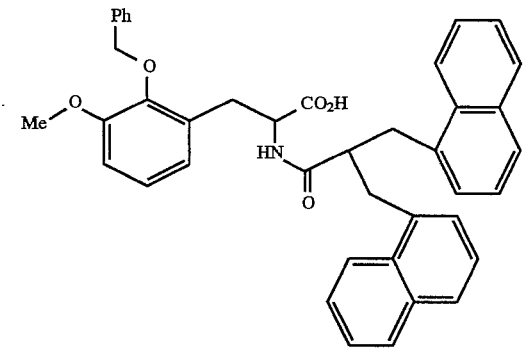

(R,S)-3-(2-Benzyloxy-3-methoxyphenyl)-2-(3-naphthalen-1-yl-2-naphthalen-1-ylmethylpropionylamino)propionic acid Preparation of intermediate ester: The ethyl ester is prepared from (R, S)-3-methoxy-2-(phenyl-methoxy) phenylalanine, ethyl ester of Example 1 and bis(1-naphthylmethyl)acetyl chloride (J. Med. Chem. 1992;35:1032–1042) by a procedure similar to that used to prepare the compound of Example 2; tlc (1:1 ethyl acetate-hexane), one spot Rf 0.7;

Mass spectrum (CI) 652 ($M^+$+1). Hydrolysis of intermediate ester: The above ester is base hydrolyzed by a procedure similar to that used in Example 5 to give pure crystalline product; mp 150°–152° C.;

Mass spectrum (CI) 624 ($M^+$+1).

Anal. Calcd for $C_{41}H_{37}NO_5$.0.1 $H_2O$:

C, 78.72; H, 6.00; N, 2.24.

Found: C, 78.41; H, 5.98; N, 2.16.

EXAMPLE 10

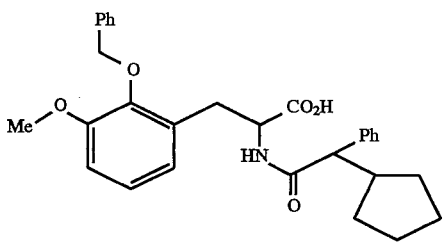

(R,S; R,S)-3-(2-Benzyloxy-3-methoxyphenyl)-2-(2-cyclopentyl-2-phenyl-acetylamino)propionic acid Preparation of intermediate ethyl ester of above: This compound is prepared from (R,S)-3-methoxy-2-(phenylmethoxy)phenylalanine, ethyl ester of Example 1 and (R,S)-a-phenylcyclopentaneacetyl chloride by a procedure similar to that in Example 2;

Mass spectrum (CI) 516 (M$^+$+1). Hydrolysis of ester: The above ester is base hydrolyzed by a procedure similar to Example 5 to give pure solid foam product as a mixture of diastereomers;

Mass spectrum (CI) 488 (M$^+$+1).

Anal. Calcd for $C_{30}H_{33}NO_5$:

C, 73.36; H, 6.85; N, 2.85.

Found: C, 73.05; H, 6.47; N, 2.74.

EXAMPLE 11

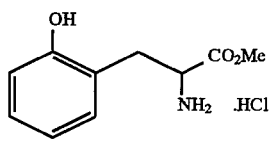

(R,S)-o-Tyrosine, methyl ester, hydrochloride

A suspension of 2.00 g (0.011 mol) of o-tryosine in 30 mL of methanol is saturated with hydrogen chloride gas, allowing the temperature to rise. The resulting solution is allowed to stand at 25° C. for 16 hours. The solution is evaporated and the remaining gum is redissolved in ca. 100 mL of methanol. Ether is added to obtain crystalline product; wt 2.31 g; mp 178°-180° C.;

Mass spectrum (CI) 196 (M$^+$+1).

EXAMPLE 12

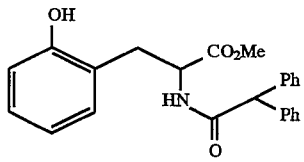

(R,S)-3-(2-Hydroxyphenyl)-2-diphenylacetylamino-propionic acid, methyl ester

A stirred and cooled (5° C.) mixture of 2.04 g (8.8 mmol) of o-tyrosine,methyl ester, hydrochloride, N,N-dimethylformamide (20 mL) and 16 g of powdered sodium bicarbonate is treated with a solution of 2.03 (8.8 mmol) of diphenylacetyl chloride in 10 mL of methylene chloride over a period of 2 minutes. The reaction mixture is then stirred at 25° for 1 hour and poured into 100 mL of ice water. The mixture is evaporated to remove the methylene chloride and the amorphous solid is filtered, washed with water, and dissolved in 100 mL of 10% methylene chloride-ether. After washing with water and 25 mL of 1N hydrochloric acid, the solution is dried (magnesium sulfate), and concentrated to give a gum. Recrystallization from 10 mL of warm ether gives 0.81 g of pure crystalline product; mp 140°-142° C.;

Mass spectrum (CI) 390 (M$^+$+1).

Anal. Calcd for $C_{24}H_{23}NO_4$:

C, 74.02; H, 5.95; N, 3.60.

Found: C, 74.26; H, 6.03; N, 3.53.

EXAMPLE 13

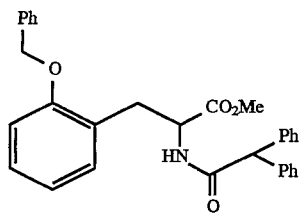

(R,S)-3-(2-Benzyloxyphenyl)-2-diphenylacetylamino-propionic acid, methyl ester

This compound is preparedby alkylation of the phenol of Example 12 with benzyl bromide by a procedure similar to that in Example 7; tlc (1:1 ethyl acetate-hexane), one spot Rf 0.85;

Mass spectrum (CI) 480 (M$^+$+1).

EXAMPLE 14

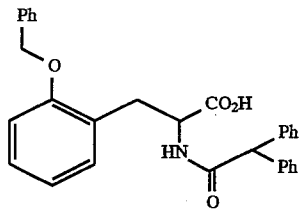

(R,S)-3-(2-Benzyloxyphenyl)-2-diphenylacetylamino-propionic acid

This compound is prepared from the corresponding methyl ester of Example 13 by a base hydrolysis similar to Example 5; mp 155°-157° C.;

Mass spectrum (CI) 466 (M$^+$+1).

Anal. Calcd for $C_{30}H_{27}NO_4$:

C, 77.40; H, 5.85; N, 3.01.

Found: C, 77.21; H, 5.98; N, 3.21.

EXAMPLE 15

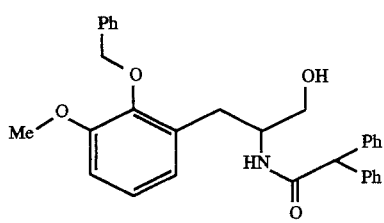

(R,S)-N-[2-(2-Benzyloxy)-3-methoxyphenyl)-1-hydroxy-methylthyl]-2,2-diphenylacetamide A quantity of 0.022 g (1.0 mol) of lithium borohydride is added portionwise at 25° C. to a stirred solution of 0.080 g (0.15 mol) of (R,S)-3-(2-benzyloxy-3-methoxyphenyl)-2-diphenylacetylaminopropionic acid, ethyl ester of Exile 2, in 3 mL of tetrahydrofuran. After 1 hour, the reaction mixture is cooled in an ice bath and ca. 0.25 mL of acetone is added. After 5 minutes, the solvent is evaporated and water (2 mL) is added. The separated gum is extracted into 15 mL of methylene chloride. The dried (potassium carbonate) solution is concentrated to give a solid.

Recrystallization from ether gives 0.68 g of pure product; mp 96°–98° C.;

Mass spectrum (CI) 482 (M$^+$+1).

Anal. Calcd for $C_{31}H_{31}NO_4$:
C, 77.31; H, 6.49; N, 2.91.

Found: C, 76.96; H, 6.43; N, 2.96.

EXAMPLE 16

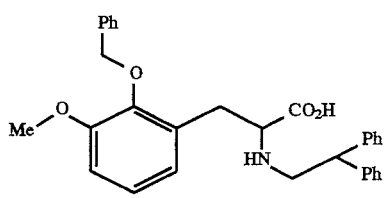

(R,S)-3-(2-Benzyloxy-3-methoxyphenyl)-2-(2,2-diphenyl-ethylamino)propionic acid

A quantity of 5.0 g of 4 A molecular sieves (powdered and freshly dried) is added to a solution of 0.260 g (0.78 mmol) of (R,S)-3-methoxy-2-(phenyl-methoxy)phenylalanine, ethyl ester base of Example 1 and 0.153 g (0.78 mmol) of diphenylacetaldehyde in 20 mL of 2-propanol. The mixture is stirred at 25° overnight and the sieves are filtered. A pinch of bromocresol green indicator is added to the filtrate. Ethereal hydrogen chloride is added dropwise until the blue color just turns green. With stirring, a quantity of 62 mg (1.0 mmol) of sodium cyanoborohydride is added portionwise over 5 minutes, adjusting the pH to green periodically with ethereal hydrogen chloride. The solution is stirred for 6 hours adjusting pH to green when necessary. After standing for 2 days, the reaction solution is evaporated. Saturated sodium bicarbonate is added and the oil is extracted into 50 mL of ether. Evaporation of the ether solution gives the ester of the product as a gum; Mass spectrum (CI) 510 (M$^+$). This material is hydrolyzed as follows: A solution of 0.143 g (0.28 mmol) of the above ester in 10 mL of methanol and exactly 1.4 mL of 1N sodium hydroxide is heated on the steam bath for 0.5 hour, allowing methanol to distill over. Water (10 mL) is added to redissolve the separated oily sodium salt. 1N Hydrochloric acid (exactly 1.4 mL) is added to precipitate the crude amino acid. Ether (5 mL) is added and the entire mixture is filtered. The cake is washed alternately with water and ether to give 81 mg of solid product. Recrystallization from 2-propanol gives pure crystals; mp 92°–95° C.;

Mass spectrum (CI) 482 (M$^+$+1).

Anal. Calcd for $C_{31}H_{31}NO_4 \cdot 0.5\ C_3H_8O \cdot H_2O$:
C, 73.70; H, 7.03; N, 2.65.

Found: C, 73.53; H, 6.63; N, 2.55.

EXAMPLE 17

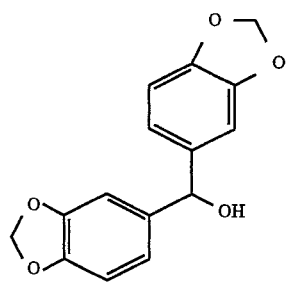

Bis-benzo [1.3 ]dioxol- 5-yl-methanol

A solution of 4-bromo-1,2-(methylenedioxy)benzene (5.02 g, 2.5 mmol) in 100 mL of dry tetrahydrofuran is cooled to –78° C. n-Butyllithium (15.6 mL, 2.5 mmol) is added dropwise to the reaction. The white suspension is stirred for another hour. Piperonal (4.12 g, 2.4 mmol) in 20 mL of tetrahydrofuran is added. The reaction is warmed to room temperature and stirred overnight. Water (50 mL) is added to quench the reaction. Layers are separated and the aqueous phase is extracted with 3×40 mL of ethyl acetate. The combined organics are dried (magnesium sulfate) and filtered. Solvent is removed in vacuo and the residue is purified by silica gel chromatography eluting with 20% ethyl acetate-hexane to give 6.1 g (90%) of product as a white solid;

Mass spectrum (CI) 255 (M$^+$+1).

EXAMPLE 18

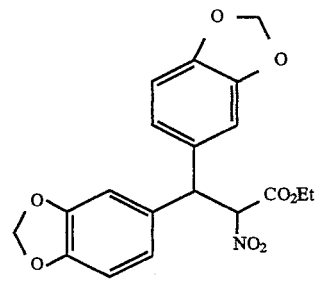

3.3-Bis-benzo [1.3]dioxol-5-yl-2-nitropropionic acid, ethyl ester

The alcohol of Example 17 is dissolved in 5 mL of nitro ethyl acetate. A catalytic amount of p-toluene-sulfonic acid is added and the reaction mixture is heated to 120° C. for 3 hours. Excess nitro ethyl acetate is removed by distillation and the residue is purified by silica gel chromatography eluting with 15% ethyl acetate-hexane to give 2.25 g (79%) of product as a yellow oil;

NMR (300 MHz, CDCl₃): d 6.73 (m, 6H), 5.94 (s, 4H), 5.78 (d, 1H), 4.86 (d, 1H), 4.12 (q, 2H), 1.11 (t, 3H).

EXAMPLE 19

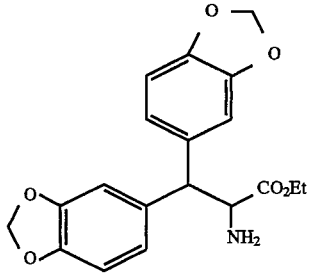

2-Amino-3,3 -bis-benzo [1,3]dioxol-5-yl-propionic acid, ethyl ester

The nitro compound of Example 18 (2.1 g, 5.42 mmol) is dissolved in 50 mL of ethyl acetate aided by a few drops of methanol. A catalytic amount of 20% palladium-on-carbon is added and the reaction mixture is stirred under one atmosphere of hydrogen at room temperature for 2 hours. The catalyst is removed by filtration through Celite and washed with ethyl acetate. The solvent is evaporated to provide 1.3 g (67%) of product as a thick oil;

Mass spectrum (CI) 358 (M⁺+1).

EXAMPLE 20

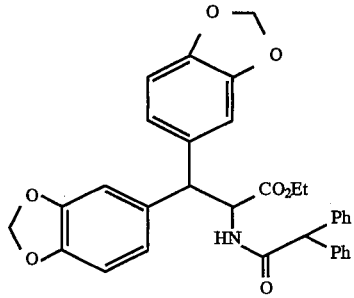

3,3-Bis-benzo[1,3]dioxol-5-yl-2-diphenylacetylamino-propionic acid, ethyl ester

The amino ester of Example 19 (0.510 g, 1.43 mmol) is mixed with diphenylacetyl chloride (0.346 g, 1.5 mmol) in 20 mL of dry chloroform. Triethylamine (0.6 mL, 4.3 mmol) is added to the reaction mixture and it is stirred for 2 hours. The solvent is evaporated and the residue is taken up into 75 mL of ethyl acetate. The solution is washed with 1N hydrochloric acid and saturated sodium bicarbonate respectively. The organic phase is dried (magnesium sulfate), filtered and purified by a short column to afford 0.552 g (70%) of product as a white solid;

Mass spectrum (CI) 552 (M⁺+1).

EXAMPLE 21

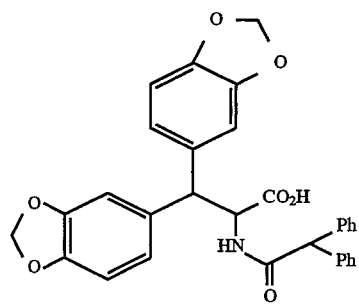

3,3 -Bis-benzo[1,3]dioxol-5-yl -2-diphenylacetylamino-propionic acid

The ester of Example 20 (0.470 g, 0.85 mmol) is dissolved in 100 mL of methanol. The solution is treated with 4.5 mL of 1N aqueous sodium hydroxide and stirred under reflux for 6 hours. Another 4.5 mL of 1N sodium hydroxide is added and reflux is continued for 24 hours. The methanol is evaporated in vacuo and the residue is dissolved in water. The solution is washed with ether, acidified with 3N hydrochloric acid and extracted with ethyl acetate (3×50 mL). The organic phase is dried (magnesium sulfate), filtered, and evaporated to give 0.407 g (91%) of product as a white solid;

Mass spectrum (CI) 524 (M⁺).

EXAMPLE 22

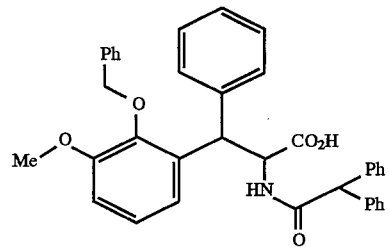

(R,S:R,S)-3-(2-Benzyloxy-3-methoxyphenyl)-2-diphenyl-acetylamino-3-phenylpropionic acid This compound is synthesized by a sequence of reactions similar to those of Examples 17 to 21 starting from 2-benzyloxy-3-methoxybenzaldehyde (U.S. Pat. No. 5,246,943) and phenyl lithium.

EXAMPLE 23

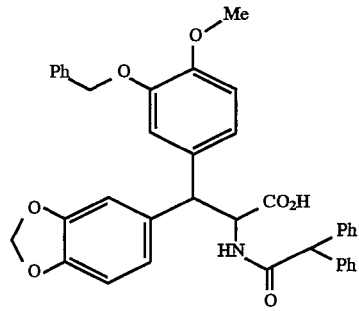

(R,S: R,S)-3-Benzo[1,3]dioxol-5-yl-3-(3-benzyloxy-4-methoxyphenyl)-2-diphenyl-acetylaminopropionic acid This compound is synthesized by a sequence of reactions similar to those of Examples 17 to 21 starting from 4-bromo- 1,2-(methylenedioxy)benzene and 3-benzyloxy-4- methoxybenzaldehyde.

EXAMPLE 24

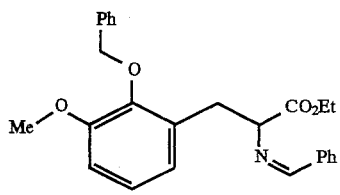

2-(Benzylideneamino)-3-(2-benzyloxy-3-methoxyphenyl)-propionic acid, ethyl ester A solution of 3.65 g (0.01 mol) of (R,S)-3-methoxy-2-(phenylmethoxy)phenylalanine, ethyl ester, hydrochloride of Example 1 is dissolved in 10 mL of water. With ice bath cooling, excess 10% potassium carbonate solution is added to pH 10. The separated oily free aminoester base is extracted into 30 mL of ethyl acetate and the solution is dried (potassium carbonate) and evaporated. A solution of the above prepared free base (ca. 0.01 mol) and 1.06 g (0.01 mol) of benzaldehyde in 30 mL of dry tetrahydrofuran is treated with 10 g of anhydrous magnesiums sulfate. The mixture is stirred at 25° C. for 28 hours. The solids are removed by filtration and the solvent is evaporated to give the product which is purified by chromatography and used directly in the next step, Example 25.

EXAMPLE 25

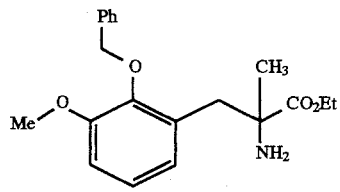

(R,S)-2-Amino-3-(2-benzyloxy-3-methoxyphenyl)-2-methyl-propionic acid, ethyl ester A solution of 1.01 g (0.01 mol) of diisopropyl-amine in 30 mL of dry tetrahydrofuran is cooled to −10° C. under nitrogen. With stirring, 4.0 mL (0.01 mol) of 2.5M n-butyl-lithium is added by cannula over 15 minutes, keeping the temperature below 0° C. The solution is stirred for 30 minutes and cooled to −12° C. A solution of ca. 0.01 mol of the schiff base of Example 24 in 20 mL of dry tetrahydrofuran is added over 30 minutes, keeping the temperature at −12° and −5° C. The solution is stirred at −5° to 0° C. for 30 minutes. Iodomethane (1.56 g, 0.011 mol) is added cautiously over 15 minutes. Stirring at room temperature is maintained for 14 hours. Water (5 mL) is cautiously added dropwise and the mixture is evaporated. With stirring, ether (30 mL) and then 3.0 g of citric acid in 20 mL of water are added to give pH of 4.2. The aqueous phase is separated and washed with 20 mL of ether. The aqueous phase is added to a cold (5° C.) saturated potassium carbonate solution (20 mL). The separated oily amino ester base is extracted into 30 mL of ethyl acetate. The solution is dried (potassium carbonate) and evaporated to give the product.

EXAMPLE 26

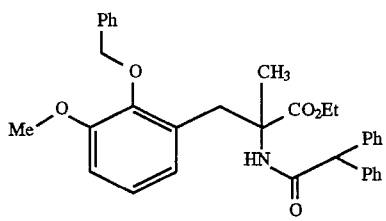

(R,S)-3-(2-Benzyloxy-3-methoxyphenyl)-2-diphenylacetylamino-2-methylpropionic acid, ethyl ester This compound is synthesized from (R,S)-2-amino-3-(2-benzyloxy-3-methoxyphenyl)-2-methylpropionic acid, ethyl ester of Example 25 and diphenylacetyl chloride by an acylation procedure similar to that in Example 2.

EXAMPLE 27

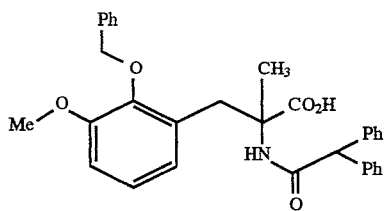

(R,S)-3-(2-Benzyloxy-3-methoxyphenyl)-2-diphenylacetylamino-2-methylpropionic acid This compound is synthesized from (R,S)-3-(2-benzyloxy-3-methoxyphenyl)-2-diphenylacetylamino-2-methylpropionic acid, ethyl ester of Example 26 by a base hydrolysis similar to that in Example 5.

EXAMPLE 28

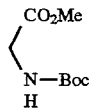

N-Boc-glycine, methyl ester

Triethylamine (25 mL) is added to a solution of 10.0 g (0.08 mol) of glycine, methyl ester, hydrochloride in 100 mL of methylene dichloride. The mixture is stirred for 20 minutes and filtered to remove the precipitate. A quantity of 17.5 g (0.08 mol) of di-tert-butyl dicarbonate is added to the filtrate and the reaction is stirred overnight. The solution is washed successively with 100 mL of 1N hydrochloric acid, 100 mL of saturated sodium bicarbonate solution and 180 mL of brine and then dried (magnesium sulfate) and evaporated to give 12.9 g (86%) of pure product;

Mass spectrum (APCI) 190 (M$^+$+1).

Anal. Calcd for $C_8H_{15}NO_4$:

C, 50.78; H, 7.99; N, 7.40.

Found: C, 51.04; H, 7.76; N, 7.01.

EXAMPLE 29

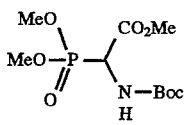

tert-Butoxycarbonylamino-(dimethoxyphosphoryl) acetic acid, methyl ester

A quantity of 2.92 g (0.016 mol) of N-bromo succinimide is added to 2.82 g (0.015 mol) of N-Boc glycine, methyl ester in 230 mL of carbon tetrachloride. The mixture is heated at reflux with stirring for 1 hour, cooled to 0° C., and filtered. The filtrate is evaporated to dryness and the residue is dissolved in 30 mL of tetrahydrofuran. A quantity of 2.10 g (0.017 mol) of trimethyl phosphite is added and the solution is maintained at reflux for 18 hours. The solvent is evaporated and the product is purified by silica gel chromatography eluting with ethyl acetate; wt 2.80 g (63%);

Mass spectrum (CI) 298 (M$^+$+1).

Anal. Calcd for $C_{10}H_{20}NO_7P$:

C, 40.41; H, 6.78; N, 4.71.

Found: C, 40.11; H, 6.49; N, 4.80.

EXAMPLE 30

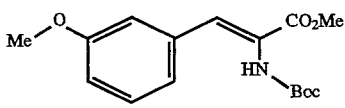

2-tert-Butoxycarbonylamino-3-(3-methoxyphenyl) acrylic acid, methyl ester

A solution of 0.70 mL (4.7 mmol) of 1,8-diazabicyclo [5.4.0.]undec-7-ene (DBU) and 1.40 g (4.7 mmol) of tert-butoxycarbonylamino-(dimethoxyphosphoryl)acetic acid, methyl ester of Example 29 in 14 mL of methylene chloride is stirred at room temperature for 25 minutes. A quantity of 0.64 g (4.7 mmol) of 3-methoxybenzaldehyde is added and the solution is stirred at room temperature overnight. Methylene chloride (100 mL) is added and the solution is washed with 80mL of 1N hydrochloric acid and then with 80 mL of brine. The dried (magnesium sulfate) organic phase is evaporated and the product is purified by silica gel chromatography, eluting with 18% ethyl acetate to give pure product as a white powder; wt 1.25 g (86%);

Mass spectrum (CI) 307 (M$^+$) and 308 (M$^+$+1).

Anal. Calcd for $C_{16}H_{21}NO_5$:

C, 62.53; H, 6.89; N, 4.56.

Found: C, 62.84; H, 6.90; N, 4.59.

EXAMPLE 31

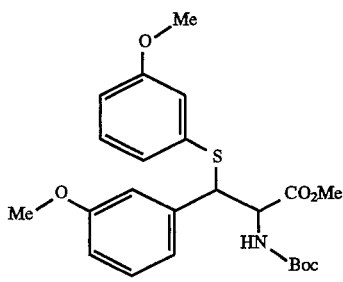

(R,S: R,S)-2-tert-Butoxycarbonylamino-3-(3-methoxyphenyl)-3-(3-methoxyphenyl-sulfanyl) propionic acid, methyl ester A solution of 0.091 g (0.65 mmol) of 3-methoxy-benzenethiol in 4 drops of piperidine is stirred at room temperature for 5 minutes. A quantity of 0.200 g (0.65 mmol) of 2-tert-butoxycarbonylamino-3-(3-methoxyphenyl)acrylic acid, methyl ester of Example 30 is added and the solution is heated at 60° C. for 24 hours. Ethyl acetate (120 mL) is added and the solution is washed with 3×80 mL of 1N sodium hydroxide and brine (80 mL). After drying (magnesium sulfate), the solution is evaporated and the residue is purified by silica gel chromatography, eluting with 20% ethyl acetate-hexane to give the product as an inseparable mixture of diastereomers; wt 0.26 g (89%);

Mass spectrum (CI) 348 (M$^+$+1-Boc).

Anal. Calcd for $C_{23}H_{29}NO_6S$:

C, 61.72; H, 6.53; N; 3.13.

Found: C, 61.34; H, 6.55; N, 3.03.

EXAMPLE 32

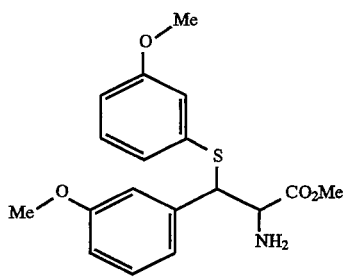

(R,S; R,S)-2-Amino-3-(3-methoxyphenyl)-3-(3-methoxyphenylsulfanyl)propionic acid, methyl ester A solution of 0.110 g (0.25 mmol) of (R,S; R,S)-2-tert-butoxycarbonylamino-3-(3-methoxyphenyl)-3-(3-methoxyphenyl-sulfanyl) propionic acid, methyl ester of Example 31 and 0.75 mL of trifluoroacetic acid in 2 mL of methylene chloride is stirred at room temperature for 30 minutes. The solvent is evaporated ant the residue is dissolved in 100 mL of ethyl acetate. The solution is washed with 2×80 mL of 1N sodium hydroxide and 80 mL of brine and then dried (magnesium sulfate) and evaporated to give the product as a mixture of diastereomers which is used in the next step without further purification; wt 0.084 g (94%); tlc (ethyl acetate/silica gel) one spot Rf 0.4;

Mass spectrum (CI) 348 (M$^+$+1).

EXAMPLE 33

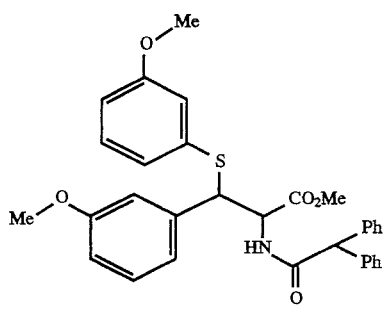

(R,S; R,S)-2-Diphenylacetylamino-3-(3-methoxyphenyl)-3-(3-methoxyphenyl-sulfanyl) propionic acid, methyl ester A solution of 0.94 g (2.7 mmol) of (R,S; R,S)-2-amino-3-(3-methoxyphenyl)-3-(3-methoxyphenyl-sulfanyl) propionic acid, methyl ester of Example 32, 15 mL of methylene dichloride, 0.69 g (3.2 mmol) of diphenylacetic acid, 0.62 g (3.2 mmol) of 1-(3-dimethylaminopropyl)-3-ethylcarbodiimide (EDAC), and 0.02 g (0.16 mmol) of 4-dimethylaminopyridine (DMAP) is stirred at room temperature for 18 hours. The reaction solution is diluted with 100 mL of methylene dichloride, washed with 80 mL of 1N sodium hydroxide and then 80 mL of 1N hydrochloric acid, dried (magnesium sulfate), and evaporated. The residue is purified via silica gel chromatography eluting with 25% ethyl acetate-hexane to give the product as an inseparable mixture of diastereomers; wt 1.10 g (90%);

Mass spectrum (CI) 542(M$^+$+1).

Anal. Calcd for $C_{32}H_{31}NO_5S$:

C, 70.96; H, 5.77; N, 2.59.

Found: C, 70.65; H, 5.86; N, 2.46.

EXAMPLE 34

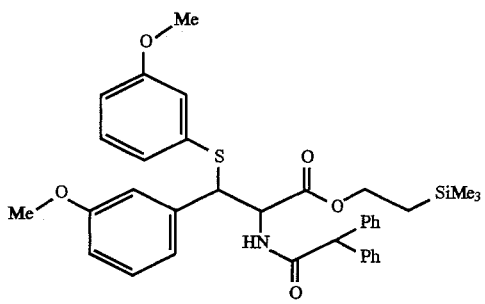

(R,S: R,S)-2-Diphenylacetylamino-3-(3-methoxyphenyl)-3-(3-methoxyphenyl-sulfanyl) propionic acid, 2-trimethyl-silylethyl ester A solution of 0.49 g (0.90 mmol) of (R,S; R,S)-2-diphenylacetylamino-3-(3-methoxyphenyl)-3-(3-methoxyphenyl-sulfanyl) propionic acid, methyl ester of Example 33, 10 mL of 2-(trimethylsilyl)ethanol and 0.77 g (2.7 mmol) of titanium(IV) isopropoxide is heated at 100° C. for 18 hours. Ether (100 mL) is added and the solution is washed with 2×80 mL of 1N hydrochloric acid and 80 mL of brine. The organic phase is dried (magnesium sulfate) and evaporated in vacuo to remove all volatiles. The residue is purified by silica gel chromatography eluting with 25% ethyl acetate-hexane to give the product; wt 0.46 g (83%);

Mass spectrum (CI) 628 (M$^+$).

Anal. Calcd for $C_{36}H_{41}NO_5SSi$:

C, 68.87; H, 6.58; N, 2.23.

Found: C, 68.84; H, 6.72; N, 2.13.

EXAMPLE 35

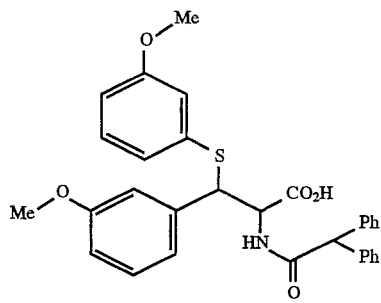

(R,S; R,S)-2-Diphenylacetylamino-3-(3-methoxyphenyl)-3-(3-methoxyphenyl-sulfanyl) propionic acid A solution of 0.40 g (0.65 mmol) of (R,S; R,S)-2-diphenylacetylamino-3-(3-methoxyphenyl)-3-(3-methoxyphenyl-sulfanyl) propionic acid, 2-trimethylsilylethyl ester of Example 34, 3.3 mL of N,N-dimethylformamide and 3.3 mL (3.3 retool) of 1M tetrabutylammonium fluoride in tetrahydrofuran is stirred at room temperature for 30 minutes. Ethyl acetate (100 mL) is added and the solution is washed with 80 mL of 1N hydrochloric acid and 80 mL of brine, dried (magnesium sulfate) and evaporated to give the product; wt 0.31 g (92%). Recrystallization from ethyl acetate-heptane gives product as a 9:1 mixture of diastereomers by NMR and hplc;

Mass spectrum (APCI) 527 (M$^+$)

EXAMPLE 36

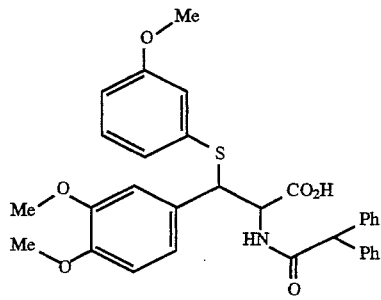

(R,S; R,S)-3-(3,4-Dimethoxyphenyl)-2-diphenylacetylamino-3-(3-methoxyphenyl-sulfanyl) propionic acid This compound is synthesized from veratraldehyde and the phosphonic acid ester of Example 29 by a procedure similar to that described in Examples 30 to 35.

EXAMPLE 37

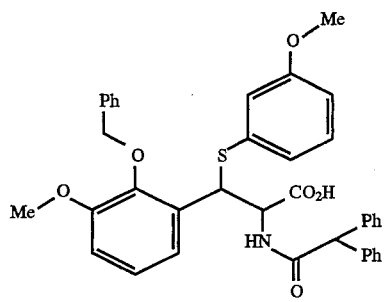

(R,S; R,S)-3-(2-Benzyloxy-3-methoxyphenyl)-2-diphenyl-acetylamino-3-(3-methoxyphenylsulfanyl) propionic acid This compound is synthesized from 2-benzyloxy-3-methoxybenzaldehyde and the phosphonic acid ester of Example 29 by a sequence of reactions similar to Examples 30 to 35.

EXAMPLE 38

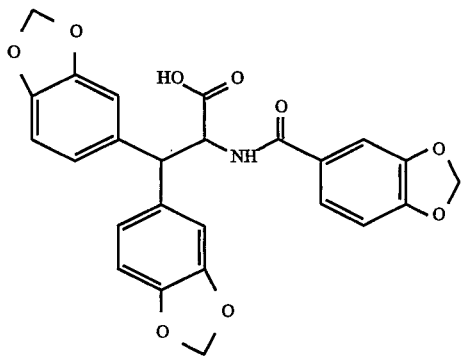

(R,S)-2-[(Benzo[1,3]dioxole-5-carbonyl)-amino]-3,3-bis-benzo [1,3]dioxol-5-yl-propionic acid This compound is prepared by acylation of the amino ester of Example 19 with 3,4-methylenedioxy-benzoyl chloride using a procedure similar to that of Example 20. Subsequent ester hydrolysis similar to that of Example 21 yields the product;

Mass spectrum (CI) 478 (M$^+$+1).

Anal. Calcd for $C_{25}H_{19}NO_9$:

C, 62.89; H, 4.01; N, 2.93.

Found: C, 60.15; H, 4.10; N, 2.80.

EXAMPLE 39

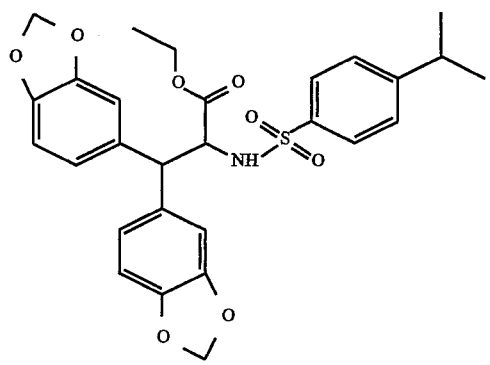

(R,S)-3,3-Bis-benzo[1,3]dioxol-5-yl-3-(4-isopropyl-benzenesulfonylamino)-propionic acid, ethyl ester This compound is prepared by acylation of the amino ester of Example 19 with 4-isopropyl-benzenesulfonyl chloride using a procedure similar to that of Example 20;

Mass spectrum (CI) 540 (M$^+$+1).

Anal. Calcd for $C_{28}H_{29}NO_8S$:

C, 62.33; H, 5.42; N, 2.60.

Found: C, 62.26; H, 5.47; N, 2.48.

EXAMPLE 40

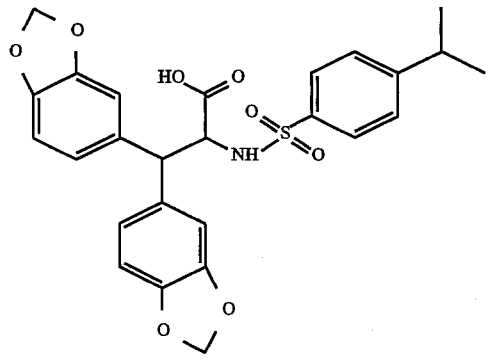

(R,S)-3,3-Bis-benzo[1,3]dioxol-5-yl-2-(4-isopropyl-benzenesulfonylamino)-propionic acid This compound is prepared by a base hydrolysis of the compound of Example 39 by a procedure similar to that of Example 21;

Mass spectrum (CI) 512 (M$^+$+1).

Anal. Calcd for $C_{26}H_{25}NO_8S$:

C, 61.25; H, 5.99; N, 2.26.

Found: C, 61.05; H, 4.93; N, 2.76.

We claim:
1. A compound of Formula I

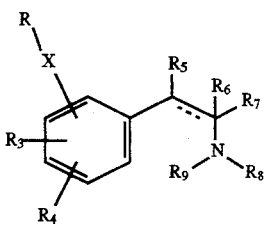

or a pharmaceutically acceptable salt thereof wherein:
R is

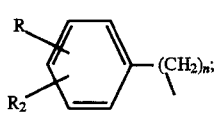

$R_1$ and $R_2$ are each independently hydrogen, lower alkyl, alkoxy, alkylthio, amino, dimethylamino, and nitro, or $R_1$ and $R_3$ when taken together form

t=1,2;

n is an integer of from 0 to 3;

X is absent, O, S, or NH;

$R_3$ and $R_4$ are each independently hydrogen, alkoxy, aryloxy, or halogen or when taken together $R_3$ and $R_4$ form

t=1,2;

$R_5$ is hydrogen, 3,4-dimethoxyphenyl, 3-benzyloxy-4-methoxyphenyl or $Y_{10}$ wherein Y is S, $(CH_2)_p$ wherein p is 0 and $R_{10}$ is methylenedioxyphenyl or 3-methoxypheny;

$R_6$ is hydrogen or is absent;

$R_7$ is $CO_2R_6$;

$R_8$ is $COR_{14}$ where $R_{14}$ is diphenylmethyl, 3,4-methylenedioxyphenyl, phenylcyclopentylmethyl, or $NR_{15}R_{16}$ where $R_{15}$ and $R_{16}$ are aryl, substituted aryl, $R_8$ is also diaralkyl, 4-isopropyl benzenesulfonyl or $SO_2R_{14}$; and $R_9$ is hydrogen or 4-isopropylphenyl.

2. A compound according to claim 1 wherein
$R_1$ and $R_2$ are each independently hydrogen, methoxy, or nitro;
n is an integer of from 0 to 3
X is O;
$R_3$ and $R_4$ are each independently hydrogen or methoxy; or R3 and $R_4$ when taken together fom methylenedioxy;
$R_5$ is hydrogen, 3,4-methylenediophenyl, 3,4-dimethoxyphyl, 3-benzyloxy-4-methoxphenyl, or 3-methoxphenylthio;

$R_6$ is hydrogen or is absent;
$R_7$ is COOH;
$R_8$ is $COR_{14}$ where $R_{14}$ is diphenylmethyl, 3,4-methylenediophenyl, phenylcyclopentylmethyl, or $NR_{15}R_{16}$ where $R_{15}$ and $R_{16}$ are phenyl, $R_8$ is also 1,1-diphenylethyl or 4-isopropyl-benzenesulfonyl; and
$R_9$ is hydrogen.

3. A compound selected from
3,3-Bis-benzo[1,3]dioxol-5-yl-2-diphenyl-acetylaminopropionic acid;

(R,S; R,S)-3-Benzo[1,3]dioxol-5-yl-3-(3-benzyloxy-4-methoxyphenyl)-2-diphenyl-acetyl-aminopropionic acid; and, (R,S; R,S)-2-Diphenylacetyl-amino-3-(3-methoxyphenyl)-3-(3-methoxyphenyl-sulfanyl) propionic acid.

4. A compound selected from 3,3-Bis-benzo[1,3]dioxol-5-yl-2-nitro-propionic acid, ethyl ester;

2-Amino-3,3-bis-benzo[1,3]dioxol-5-yl-propionic acid, ethyl ester;

3,3-Bis-benzo[1,3]dioxol-5-yl-2-diphenyl-acetylaminopropionic acid, ethyl ester;

(R,S)-3-(2-Benzyloxy-3-methoxyphenyl)-2-diphenylacetylamino-2-methylpropionic acid;

2-tert-Butoxycarbonylamino-3-(3-methoxyphenyl) acrylic acid, methyl ester;

(R,S; R,S)-2-tert-Butoxycarbonylamino-3-(3-methoxyphenyl)-3-(3-methoxyphenyl-sulfanyl)-propionic acid, methyl ester;

(R,S; R,S)-2-Amino-3-(3-methoxyphenyl)-3-(3-methoxyphenylsulfanyl)propionic acid, methyl ester; and (R,S; R,S)-2-Diphenylacetylamino-3-(3-methoxyphenyl)-3-(3-methoxyphenyl-sulfanyl)-propionic acid, methyl ester.

5. A pharmaceutical composition comprising a therapeutically effective amount of a compound of claim 1 in admixture with a pharmaceutically acceptable carrier.

6. A method of inhibiting elevated levels of endothelin comprising administering to a host in need thereof a therapeutically effective amount of a compound of claim 1 in unit dosage form.

7. A method of treating subarachnoid hemorrhage comprising administering to a host suffering therefrom a therapeutically effective amount of a compound of claim 1 in unit dosage form.

8. A method of treating essential, renovascular, malignant and pulmonary hypertension comprising administering to a host suffering therefrom a therapeutically effective amount of a compound of claim 1 in unit dosage form.

9. A method of treating congestive heart failure comprising administering to a host suffering therefrom a therapeutically effective amount of a compound of claim 1 in unit dosage form.

10. A method of treating cerebral ischemia or cerebral infarction comprising administering to a host suffering therefrom a therapeutically effective amount of a compound of claim 1 in unit dosage form.

11. A method of treating myocardial ischemia comprising administering to a host suffering therefrom a therapeutically effective amount of a compound of claim 1 in unit dosage form.

12. A compound selected from:
(R,S)-3-Methoxy-2-(phenylmethoxy)phenylalanine, ethyl ester, hydrochloride;

(R,S)-3-[2-Benzyloxy-3-methoxyphenyl)-2-diphenylacetylaminopropionic acid, ethyl ester;

(R,S)-N-(Diphenylacetyl)-3-methoxy-2-(phenylmethoxy)phenylalanine;

(R,S)=2-Diphenylacetylamino-3-[3-methoxy-2-(2-phenylethoxy)phenyl]propionic acid;

(R,S)-3-(2-Benzyloxy-3-methoxyphenyl)-2-(3.3-diphenylureido)propionic acid;

(R,S)-Diphenylacetylamino-3-[3-methoxy-2-(3-phenylpropoxy)phenyl]propionic acid;

(R,S)-2-Diphenylacetylamino-3-[3-methoxy-2-(4-nitrophenoxy)phenyl]propionic acid;

(R,S)-3-(2Benzyloxy-3-methoxyphenyl)- 2-(3-naphhhalen-1-yl-2-naphthaion-1-ylmethylpropionyl-amino) proptonic acid;

(R,S; R,S)-3-(2-Benzyloxy-3-methoxyphenyl)-2-(2-cyclopentyl-2-phenyl-acetylamino) propionic acid;

(R,S)-3-(2-Hydroxyphenyl)-2- diphenylacetylaminopropionic acid, methyl ester;

(R,S)-3-(2-Benzyloxyphenyl)-2-diphenylacetylaminopropionic acid;

(R,S; R,S)-3-Benzo[1,3]dioxol-5-yl-3-(3-benzyloxy-4-methoxyl-phenyl)-2-diphenyl-acetylaminopropionic acid;

(R,S; R,S)-2-Diphenylacetylamino-3-(3-methoxylphenyl)-3-(3-methoxyphenyl-sulfanyl) propionic acid;

(R,S) -N-2-(2-Benzyloxy-3-methoxyphenyl)-1-hydroxymethylethyl]-2,2-diphenylacetamide; and (R,S)-3-(2-Benzyloxy-3-methoxyphenyl)-2-(2,2-diphenylethylamino)propionic acid.

* * * * *